US012594067B2

(12) United States Patent     (10) Patent No.:   US 12,594,067 B2

Baril                      (45) Date of Patent:       Apr. 7, 2026

(54) ROTARY STITCHING DEVICE

(71) Applicant: Covidien LP, Mansfield, MA (US)

(72) Inventor: Jacob C. Baril, Norwalk, CT (US)

(73) Assignee: Covidien LP, Mansfield, MA (US)

( * ) Notice: Subject to any disclaimer, the term of this patent is extended or adjusted under 35 U.S.C. 154(b) by 621 days.

(21) Appl. No.: 18/149,314

(22) Filed: Jan. 3, 2023

(65)           Prior Publication Data

US 2023/0210521 A1     Jul. 6, 2023

Related U.S. Application Data

(60) Provisional application No. 63/296,762, filed on Jan. 5, 2022.

(51) Int. Cl.
*A61B 17/04*        (2006.01)
*A61B 17/00*        (2006.01)

(52) U.S. Cl.
CPC ...... *A61B 17/0469* (2013.01); *A61B 17/0491* (2013.01); *A61B 2017/00367* (2013.01)

(58) Field of Classification Search
CPC ............ A61B 17/0469; A61B 17/0491; A61B 2017/00367; A61B 17/0625; A61B 2017/2929; A61B 2017/2927
See application file for complete search history.

(56)            References Cited

U.S. PATENT DOCUMENTS

| | | |
|---|---|---|
| 1,037,864 A | 9/1912 | Carlson et al. |
| 1,131,163 A | 3/1915 | Saunders et al. |
| 1,293,565 A | 2/1919 | Smit |
| 1,449,087 A | 3/1923 | Bugbee |
| 1,876,792 A | 9/1932 | Thompson |
| 2,213,830 A | 9/1940 | Anastasi |
| 2,880,728 A | 4/1959 | Rights |
| 3,090,386 A | 5/1963 | Curtis |
| 3,349,772 A | 10/1967 | Rygg |
| 3,470,875 A | 10/1969 | Johnson |
| 3,807,407 A | 4/1974 | Schweizer |
| 3,842,840 A | 10/1974 | Schweizer |
| 3,901,244 A | 8/1975 | Schweizer |

(Continued)

FOREIGN PATENT DOCUMENTS

| | | |
|---|---|---|
| EP | 0705569 A1 | 4/1996 |
| EP | 3703578 A1 | 9/2020 |

(Continued)

*Primary Examiner* — Kathleen S Holwerda
*Assistant Examiner* — James R Mcginnity
(74) *Attorney, Agent, or Firm* — Dymera IP, LLC

(57)           ABSTRACT

A stitching device includes an end effector having first and second jaw members and first and second pins, a stationary cam, and a rotary cam. The first pin is supported on the first jaw member and the second pin is supported on the second jaw member. The stationary cam defines a first cam slot, and the rotary cam defines a second cam slot. The first and second cam slots receive the first and second pins and are configured to releasably secure one of the first or second jaw members to the rotary cam such that the first and second jaw members rotate about the stationary cam in alternating fashion. During each revolution of the rotary cam, the one of the first or second jaw members rotates with the rotary cam a substantially full revolution while the other of the first or second jaw members remains stationary.

20 Claims, 15 Drawing Sheets

(56) References Cited

U.S. PATENT DOCUMENTS

| | | | |
|---|---|---|---|
| 3,946,740 | A | 3/1976 | Bassett |
| 4,021,896 | A | 5/1977 | Stierlein |
| 4,109,658 | A | 8/1978 | Hughes |
| 4,161,951 | A | 7/1979 | Scanlan, Jr. |
| 4,164,225 | A | 8/1979 | Johnson et al. |
| 4,236,470 | A | 12/1980 | Stenson |
| 4,345,601 | A | 8/1982 | Fukuda |
| 4,373,530 | A | 2/1983 | Kilejian |
| 4,471,781 | A | 9/1984 | Di Giovanni et al. |
| 4,491,135 | A | 1/1985 | Klein |
| 4,580,567 | A | 4/1986 | Schweitzer et al. |
| 4,621,640 | A | 11/1986 | Mulhollan et al. |
| 4,635,638 | A | 1/1987 | Weintraub et al. |
| 4,890,615 | A | 1/1990 | Caspari et al. |
| 4,923,461 | A | 5/1990 | Caspari et al. |
| 4,935,027 | A | 6/1990 | Yoon |
| 4,957,498 | A | 9/1990 | Caspari et al. |
| 5,059,201 | A | 10/1991 | Asnis |
| 5,100,421 | A | 3/1992 | Christoudias |
| 5,171,257 | A | 12/1992 | Ferzli |
| 5,181,919 | A | 1/1993 | Bergman et al. |
| 5,207,693 | A | 5/1993 | Phillips |
| 5,217,471 | A | 6/1993 | Burkhart |
| 5,242,458 | A | 9/1993 | Bendel et al. |
| 5,254,126 | A | 10/1993 | Filipi et al. |
| 5,261,917 | A | 11/1993 | Hasson et al. |
| 5,281,220 | A | 1/1994 | Blake, III |
| 5,336,230 | A | 8/1994 | Leichtling et al. |
| 5,454,823 | A | 10/1995 | Richardson et al. |
| 5,674,229 | A | 10/1997 | Tovey et al. |
| 5,674,230 | A | 10/1997 | Tovey et al. |
| 5,690,652 | A | 11/1997 | Wurster et al. |
| 5,814,054 | A | 9/1998 | Kortenbach et al. |
| 5,954,733 | A * | 9/1999 | Yoon .................. A61B 18/1445 606/147 |
| 5,980,538 | A | 11/1999 | Fuchs et al. |
| 6,071,289 | A * | 6/2000 | Stefanchik ......... A61B 17/0469 606/147 |
| 6,270,508 | B1 | 8/2001 | Klieman et al. |
| 8,177,794 | B2 | 5/2012 | Cabrera et al. |
| 8,226,667 | B2 | 7/2012 | Viola et al. |
| 8,246,637 | B2 | 8/2012 | Viola et al. |
| 8,292,905 | B2 | 10/2012 | Taylor et al. |
| 8,292,906 | B2 | 10/2012 | Taylor et al. |
| 8,337,515 | B2 | 12/2012 | Viola et al. |
| 8,372,090 | B2 | 2/2013 | Wingardner et al. |
| 8,454,631 | B2 | 6/2013 | Viola et al. |
| 8,460,275 | B2 | 6/2013 | Taylor et al. |
| 8,490,713 | B2 | 7/2013 | Furnish et al. |
| 8,496,674 | B2 | 7/2013 | Cabrera et al. |
| 8,506,581 | B2 | 8/2013 | Wingardner, III et al. |
| 8,628,545 | B2 | 1/2014 | Cabrera et al. |
| 8,636,752 | B2 | 1/2014 | Cabrera et al. |
| 8,702,732 | B2 * | 4/2014 | Woodard, Jr. ..... A61B 17/0469 606/147 |
| 8,747,424 | B2 | 6/2014 | Taylor et al. |
| D708,746 | S | 7/2014 | Cabrera et al. |
| 8,864,776 | B2 | 10/2014 | Bogart et al. |
| 8,968,340 | B2 | 3/2015 | Chowaniec et al. |
| 8,968,342 | B2 | 3/2015 | Wingardner, III et al. |
| 9,113,860 | B2 | 8/2015 | Viola et al. |
| 9,271,723 | B2 | 3/2016 | Taylor et al. |
| 9,615,824 | B2 | 4/2017 | Furnish et al. |
| 9,675,340 | B2 | 6/2017 | Sniffin et al. |
| 10,806,441 | B2 | 10/2020 | Malkowski |
| 11,058,413 | B2 | 7/2021 | Malkowski et al. |
| 2004/0260314 | A1 | 12/2004 | Lizardi |
| 2005/0149066 | A1 | 7/2005 | Stafford |
| 2006/0020274 | A1 | 1/2006 | Ewers |
| 2009/0221868 | A1 | 9/2009 | Evans |
| 2009/0299406 | A1 | 12/2009 | Swain |
| 2010/0228270 | A1 | 9/2010 | Bogart et al. |
| 2011/0040308 | A1 | 2/2011 | Cabrera et al. |
| 2013/0023725 | A1 | 1/2013 | Nose |
| 2013/0282031 | A1 | 10/2013 | Woodard, Jr. et al. |
| 2017/0150961 | A1 | 6/2017 | Marczyk et al. |
| 2017/0164943 | A1 | 6/2017 | Kasahara et al. |
| 2019/0314011 | A1 * | 10/2019 | Aravalli ............. A61B 17/0625 |

FOREIGN PATENT DOCUMENTS

| | | |
|---|---|---|
| JP | H07178100 A | 7/1995 |
| JP | 2001500765 A | 1/2001 |
| JP | 2010505524 A | 2/2010 |
| JP | 2017213369 A | 12/2017 |
| WO | 0022992 A1 | 4/2000 |
| WO | 0054667 A1 | 9/2000 |
| WO | 2007033314 A2 | 3/2007 |
| WO | 2008045353 A2 | 4/2008 |

* cited by examiner

ROTARY STITCHING DEVICE

CROSS-REFERENCE TO RELATED APPLICATION

This application claims the benefit of and priority to U.S. Provisional Patent Application No. 63/296,762, filed Jan. 5, 2022, the entire contents of which is incorporated by reference herein.

FIELD

The disclosure is directed to endoscopic stitching devices and, more particularly, to endoscopic rotary stitching devices.

BACKGROUND

As medical and hospital costs continue to increase, surgeons are constantly striving to develop advanced surgical techniques. Advances in the surgical field are often related to the development of operative techniques which involve less invasive surgical procedures that reduce overall patient trauma. In this manner, the length of hospital stays can be significantly reduced, and, therefore, hospital and medical costs can be reduced as well. One surgical technique to reduce the invasiveness of surgical procedures is endoscopic surgery. Endoscopic surgery is performed with specialized instruments that are positioned through small incisions in a patient to reduce trauma to the patient and shorten patient recovery times.

Endoscopic suturing devices for suturing tissue are known. Such devices often function by transferring a needle back and forth between two jaws. Movement of the needle with known suturing devices does not mimic traditional suturing techniques performed manually with graspers and a free needle and may be awkward for a clinician. Thus, the clinician must be trained differently for suturing with traditional suturing techniques and for suturing with an endoscopic suturing device.

Accordingly, a continuing need exists in the art for an endoscopic suturing device that mimics traditional suturing techniques.

SUMMARY

This disclosure is directed to an endoscopic suturing device that mimics traditional suturing techniques.

One aspect of this disclosure is directed to a suturing device including a handle assembly, an elongate body assembly, and an end effector. The elongate body assembly is coupled to the handle assembly, defines a longitudinal axis, and includes a stationary cam and a rotary cam. The stationary cam defines a first cam slot, and the rotary cam defines a second cam slot. The rotary cam is rotatable in relation to the stationary cam through revolutions. The end effector includes a first jaw member and a second jaw member. The first jaw member supports a first pin, and the second jaw member supports a second pin. The first and second pins are received within the first and second cam slots. The first and second cam slots are configured to releasably secure one of the first or second jaw members to the rotary cam such that the first and second jaw members rotate about the stationary cam in alternating fashion. During each of the revolutions of the rotary cam, the one of the first or second jaw members rotates with the rotary cam a substantially full revolution while the other of the first or second jaw members remains stationary.

In aspects of the disclosure, the stationary cam has a tubular configuration and defines a longitudinally extending bore, and the rotary cam has a cylindrical configuration and is rotatably received within the longitudinally extending bore of the stationary cam.

In some aspects of the disclosure, the stationary cam has an inner surface that defines the first cam slot, and the rotary cam has an outer surface that defines the second cam slot.

In certain aspects of the disclosure, the stitching device includes an outer tube positioned about the stationary cam.

In aspects of the disclosure, each of the first and second jaw members includes a distal portion and a proximal portion, and the proximal portion is rotatably supported about the rotary cam.

In some aspects of the disclosure, the rotary cam includes a stepped distal portion that defines a distal step and an intermediate step that is positioned proximally of the distal step.

In certain aspects of the disclosure, the proximal portion of each of the first and second jaw members is rotatably supported on the distal step and the second cam slot is formed on the intermediate step.

In aspects of the disclosure, the proximal portion of each of the first and second jaw members defines a proximally facing shoulder and the stepped distal portion of the rotary cam defines an annular shoulder between the distal step and the intermediate step.

In some aspects of the disclosure, the proximally facing shoulders of the first and second jaw members are engaged with the annular shoulder of the rotary cam.

In certain aspects of the disclosure, the stitching device includes a jaw collar that is secured within the outer tube, and the jaw collar engages the proximal portion of the first and second jaw members to retain the proximal portion of the jaw members within the outer tube.

In aspects of the disclosure, the stitching device includes a suture needle, and each of the first and second jaw members defines a transverse bore.

In some aspects of the disclosure, the suture needle is movable between the transverse slots of the first and second jaw members.

In certain aspects of the disclosure, the stitching device includes first and second blades, and each of the first and second jaw members defines a longitudinally extending channel.

In aspects of the disclosure, the first blade is received within the longitudinally extending channel of the first jaw member and the second blade is received within the longitudinally extending channel of the second jaw member.

In some aspects of the disclosure, the first and second blades movable within the longitudinally extending channels of the first and second jaw members between retracted and advanced positions to secure the suture needle to a respective one of the first and second jaw members.

In certain aspects of the disclosure, the first pin is secured to the first blade and the second pin is secured to the second blade, and the first and second cam slots are configured to move the first and second blades between their respective retracted and advanced positions.

In aspects of the disclosure, the suture needle includes an angled cam surface and each of the first and second blades includes an angled distal end that is positioned to engage the angled cam surface of the suture needle when the first or second blade moves from the retracted position to the advanced position to translate the suture needle within the transverse bore of the first or second jaw member.

In some aspects of the disclosure, each of the first and second jaw members defines a longitudinal slot that receives one of the first and second pins.

In certain aspects of the disclosure, the stitching device includes a suture that is attached to one end of the suture needle.

Other aspects of the disclosure are directed to a suturing device including an elongate body assembly, an end effector, and a suture needle. The elongate body assembly defines a longitudinal axis and includes a stationary cam and a rotary cam. The stationary cam defines a first cam slot, and the rotary cam defines a second cam slot. The rotary cam is rotatable in relation to the stationary cam through revolutions. The end effector includes a first jaw member and a second jaw member. The first jaw member supports a first pin, and the second jaw member supports a second pin. The first and second pins are received within the first and second cam slots. The first and second cam slots are configured to releasably secure one of the first or second jaw members to the rotary cam such that the first and second jaw members rotate about the stationary cam in alternating fashion. During each of the revolutions of the rotary cam, the one of the first or second jaw members rotates with the rotary cam a substantially full revolution while the other of the first or second jaw members remains stationary. The suture needle is movable between the first and second jaw members and is securable to and movable with the one of the first or second jaw members.

Still other aspects of the disclosure are directed to a suturing device including an elongate body assembly, an end effector, a suture needle, and first and second blades. The elongate body assembly defines a longitudinal axis and includes a stationary cam and a rotary cam. The stationary cam defines a first cam slot, and the rotary cam defines a second cam slot. The rotary cam is rotatable in relation to the stationary cam through revolutions. The end effector includes a first jaw member and a second jaw member. The first jaw member supports a first pin, and the second jaw member supports a second pin. The first and second pins are received within the first and second cam slots of the stationary and rotary cams. The first and second cam slots are configured to releasably secure one of the first or second jaw members to the rotary cam such that the first and second jaw members rotate about the stationary cam in alternating fashion. During each of the revolutions of the rotary cam, the one of the first or second jaw members rotates with the rotary cam a substantially full revolution while the other of the first or second jaw members remains stationary. The suture needle is movable between the first and second jaw members and securable to and movable with the one of the first or second jaw members. Each of the first and second jaw members defines a longitudinally extending channel. The first blade is received within the longitudinally extending channel of the first jaw member and the second blade is received within the longitudinally extending channel of the second jaw member. The first and second blades are movable between retracted and advanced positions to secure the suture needle to a respective one of the first and second jaw members.

Other features of the disclosure will be appreciated from the following description.

BRIEF DESCRIPTION OF THE DRAWINGS

Various aspects of the disclosure are described herein below with reference to the drawings, wherein.

DETAILED DESCRIPTION

Figure 1:
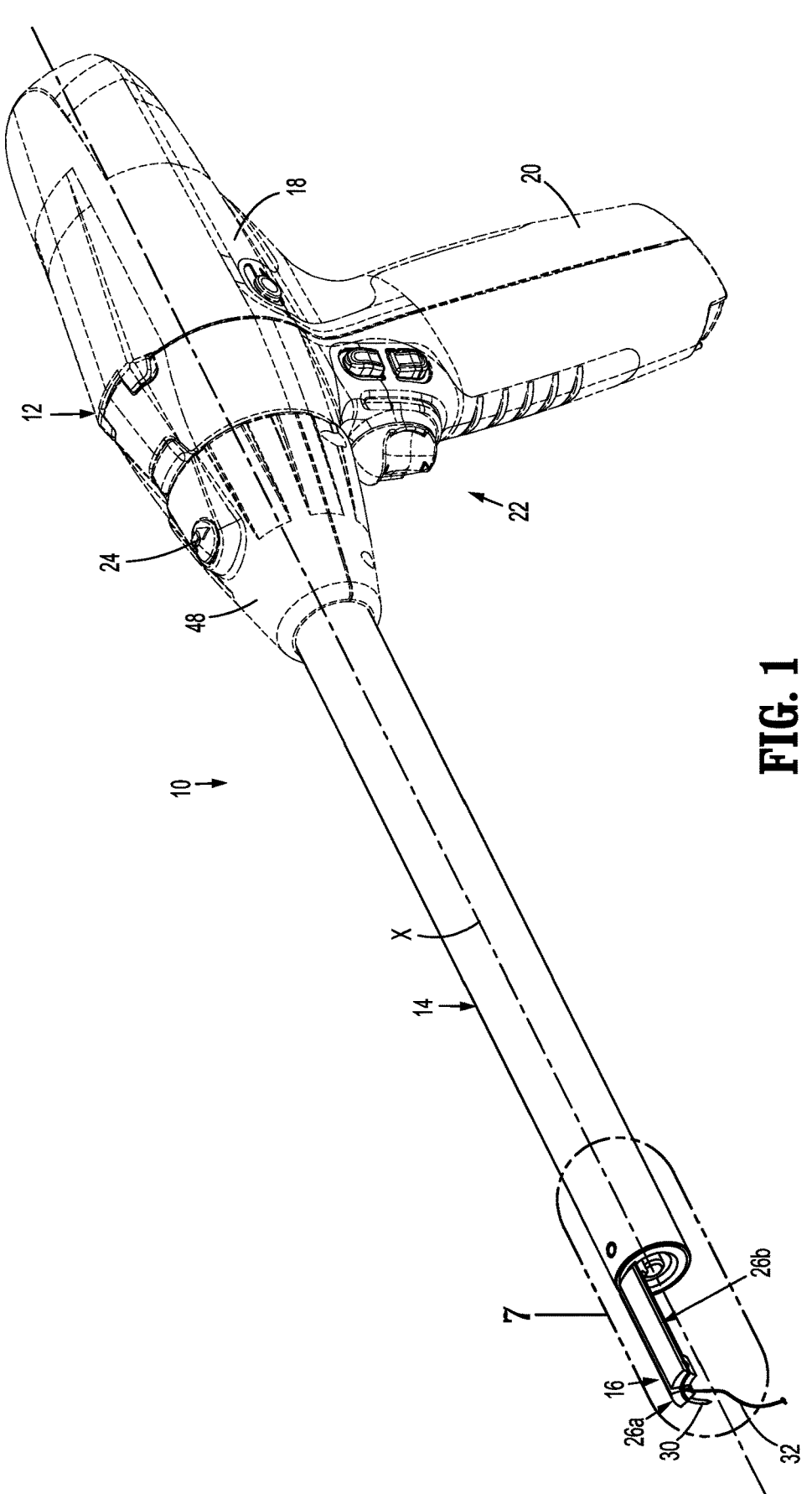
FIG. 1 is a side perspective view of a rotary stitching device according to aspects of the disclosure with a handle assembly shown in phantom.

The disclosed rotary stitching device will now be described in detail with reference to the drawings in which like reference numerals designate identical or corresponding elements in each of the several views. However, it is to be understood that aspects of the disclosure described herein are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device in its customary fashion, while the term "distal" is used generally to refer to that portion of the device that is farther from the clinician during use of the device in its customary fashion. In addition, the term "endoscopic" is used generally to refer to endoscopic, laparoscopic, arthroscopic, and/or any other procedure conducted through small diameter incision or cannula. Further, the term "clinician" is used generally to refer to medical personnel including doctors, nurses, surgeons, and support personnel. The terms "about" or "approximately" or "substantially" as used herein may be inclusive of the stated value and include an acceptable range of variation for the value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

A stitching device is described that that mimics traditional suturing techniques. The stitching device includes an end effector having first and second jaw members and first and second pins, and an elongate body assembly having a stationary cam and a rotary cam. The first pin is supported on the first jaw member and the second pin is supported on the second jaw member. The stationary cam defines a first cam slot, and the rotary cam defines a second cam slot. The first and second cam slots receive the first and second pins and are configured to releasably secure one of the first or second jaw members to the rotary cam such that the first and second jaw members rotate about the stationary cam one at a time in alternating fashion. During each revolution of the rotary cam, the jaw member releasably secured to the rotary cam rotates with the rotary cam a substantially full revolution while the other jaw member remains stationary.

FIG. 1 illustrates a rotary stitching device shown generally as stitching device 10 according to aspects of the disclosure. The stitching device 10 includes a handle assembly 12, an elongate body assembly 14, and an end effector 16. The handle assembly 12 includes a housing 18 that forms a handle grip 20 and supports actuation buttons 22 that are supported on the handle grip 20. In aspects of the disclosure, the handle assembly 10 is powered and includes an electric motor (not shown) and a battery (not shown). The actuation buttons 22 can be depressed or moved to actuate the motor to control operation of the stitching device 10 as described in detail below.

The elongate body assembly 14 defines a longitudinal axis "X" (FIG. 1) and includes a proximal portion and a distal portion. The proximal portion of the elongate body assembly 14 is coupled to the handle assembly 12 and the distal portion of the elongate body assembly 14 supports the end effector 16. In aspects of the disclosure, the elongate body assembly 14 is releasably coupled to the handle assembly 12 and includes a release button 24 that can be depressed to disengage the elongate body assembly 14 from the handle assembly 12. The end effector 16 includes a first jaw assembly 26a, a second jaw assembly 26b, a suture needle 30, and a suture 32 that is secured to one end of the suture needle 30.

Figure 2:
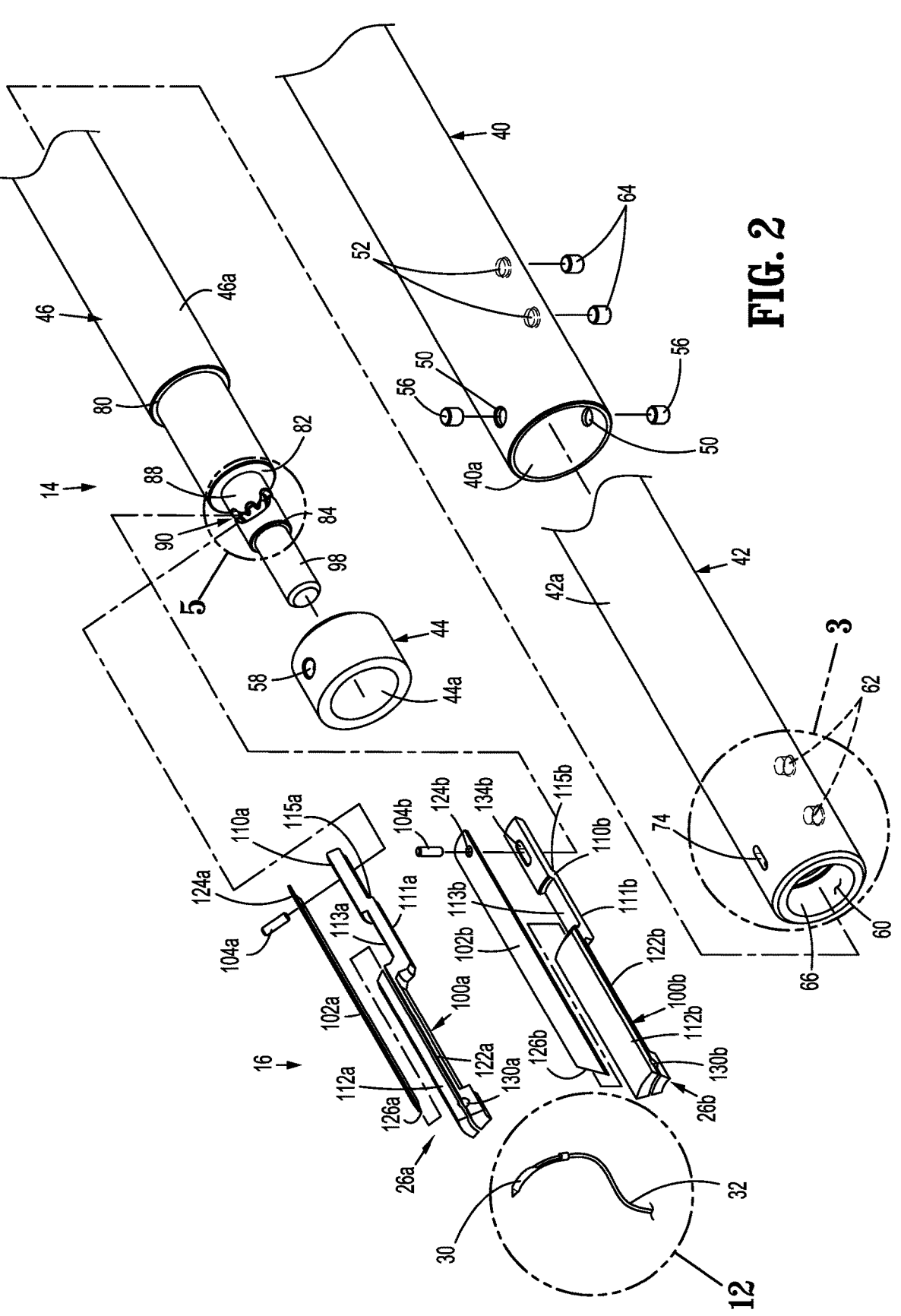
FIG. 2 is an exploded, side perspective view of the distal portion of the rotary stitching device shown in FIG. 1.

FIG. 2 illustrates the elongate body assembly 14 which includes an outer tube 40, a stationary cam 42, a jaw collar 44, a rotary cam 46, and a proximal hub portion 48 (FIG. 1). The proximal hub portion 48 of the elongate body assembly 14 supports a release mechanism (not shown) that includes the release button 24 and releasably couples the elongate body assembly 14 to the handle assembly 12 (FIG. 1).

The outer tube 40 has a proximal end portion and a distal end portion and defines a longitudinally extending bore 40a that extends between the proximal and distal end portions and receives the remaining components of the elongate body assembly 14. The distal end portion of the outer tube 40 defines openings 50 and 52. The jaw collar 44 includes a proximal end and has a cylindrical configuration that defines a longitudinal bore 44a that is axially aligned with the longitudinal bore 40a of the outer tube 40. In aspects of the disclosure, the jaw collar 44 is fixedly secured within the distal end portion of the outer tube 20 by pins or screws 56 that are received through the openings 50 in the outer tube 40 and the openings 58 (only one is shown) formed in the jaw collar 44.

Figures 3, 4:
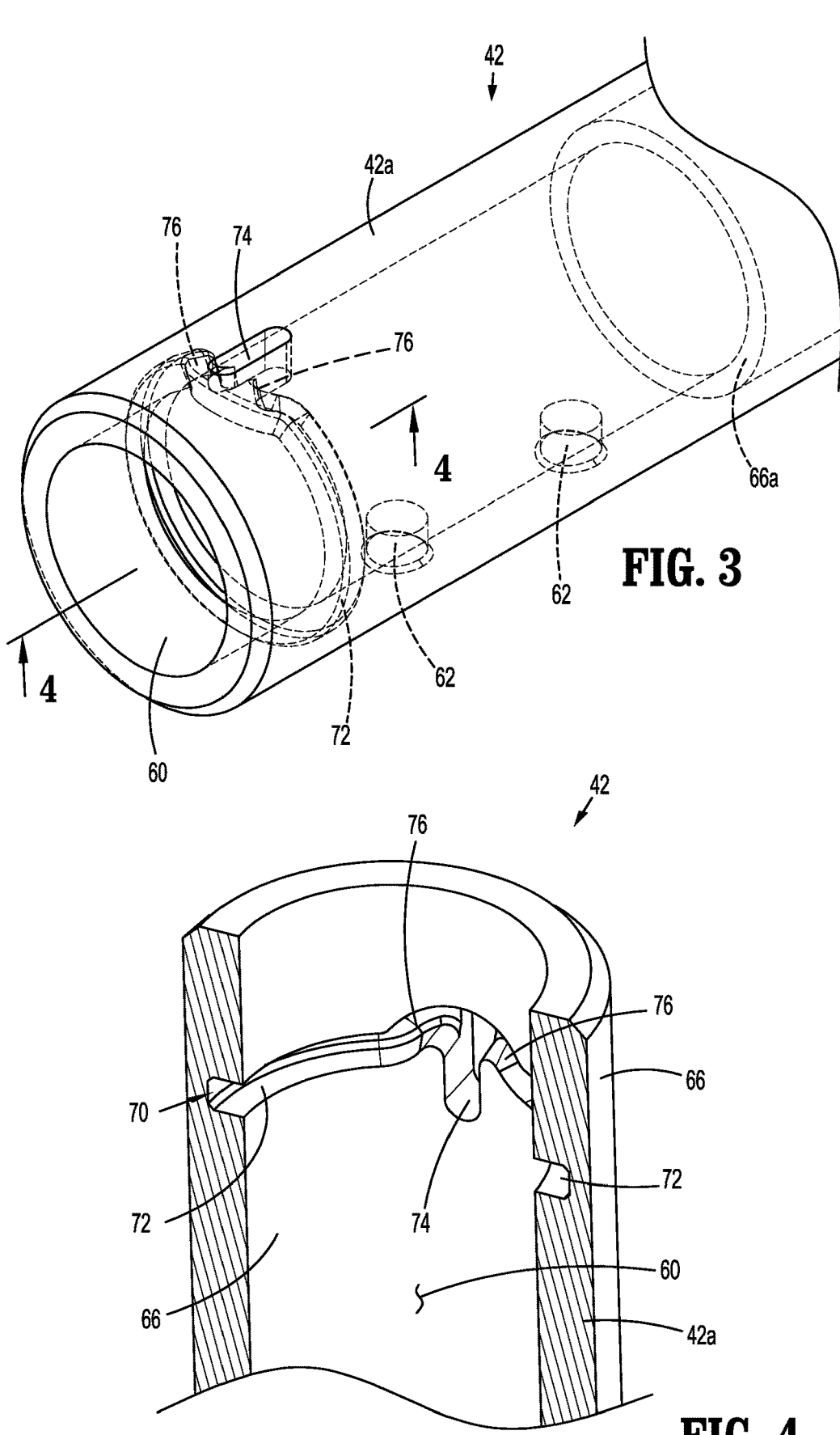
FIG. 3 is an enlarged view of the indicated area of detail shown in FIG. 2 illustrating a distal portion of a stationary cam of the rotary stitching device.
FIG. 4 is a cross-sectional view taken along section line 4-4 of FIG. 3.

FIGS. 2-4 illustrate the stationary cam 42 which includes a body 42a having a distal end and an elongated tubular configuration that defines a longitudinally extending bore 60 (FIG. 2). The body 42a of the stationary cam 42 is received within the longitudinally extending bore 40a of the outer tube 40 and defines two bores 62. The bores 62 receive pins or screws 64 (FIG. 2) that extend through the openings 52 in the outer tube 40 and into the bores 62 in the body 42a of the stationary cam 42 to fixedly secure the stationary cam 42 within the outer tube 40. In aspects of the disclosure, a distal portion of the body 42a of the stationary cam 42 has an inner wall 66 that is stepped to define an annular shoulder 66a (FIG. 3).

The inner wall 66 of the stationary cam 42 defines a first cam slot 70 that extends entirely about the longitudinally extending bore 60 defined by the stationary cam 42. The first cam slot 70 includes a circular slot portion 72, a longitudinal slot portion 74, and angled slot portions 76. The circular slot portion 72 of the first cam slot 70 extends about the majority of the circumference of the stationary cam 42 along a plane that is substantially transverse to the longitudinal axis "X" of the elongate body assembly 14. The longitudinal slot portion 74 of the first cam slot 70 extends in a direction substantially parallel to the longitudinal axis "X" of the elongate body assembly 14. The angled slot portions 76 of the first cam slot 70 extend from ends of the circular slot portion 72 to the longitudinal slot portion 74 in a direction oblique to the longitudinal axis "X" of the elongate body assembly 14. The first cam slot 70 is configured to control operation of the end effector 16 as described in further detail below. The longitudinal slot portion 74 of the first cam slot 70 may extend through the body 42a of the stationary cam 42.

Figures 5, 6:
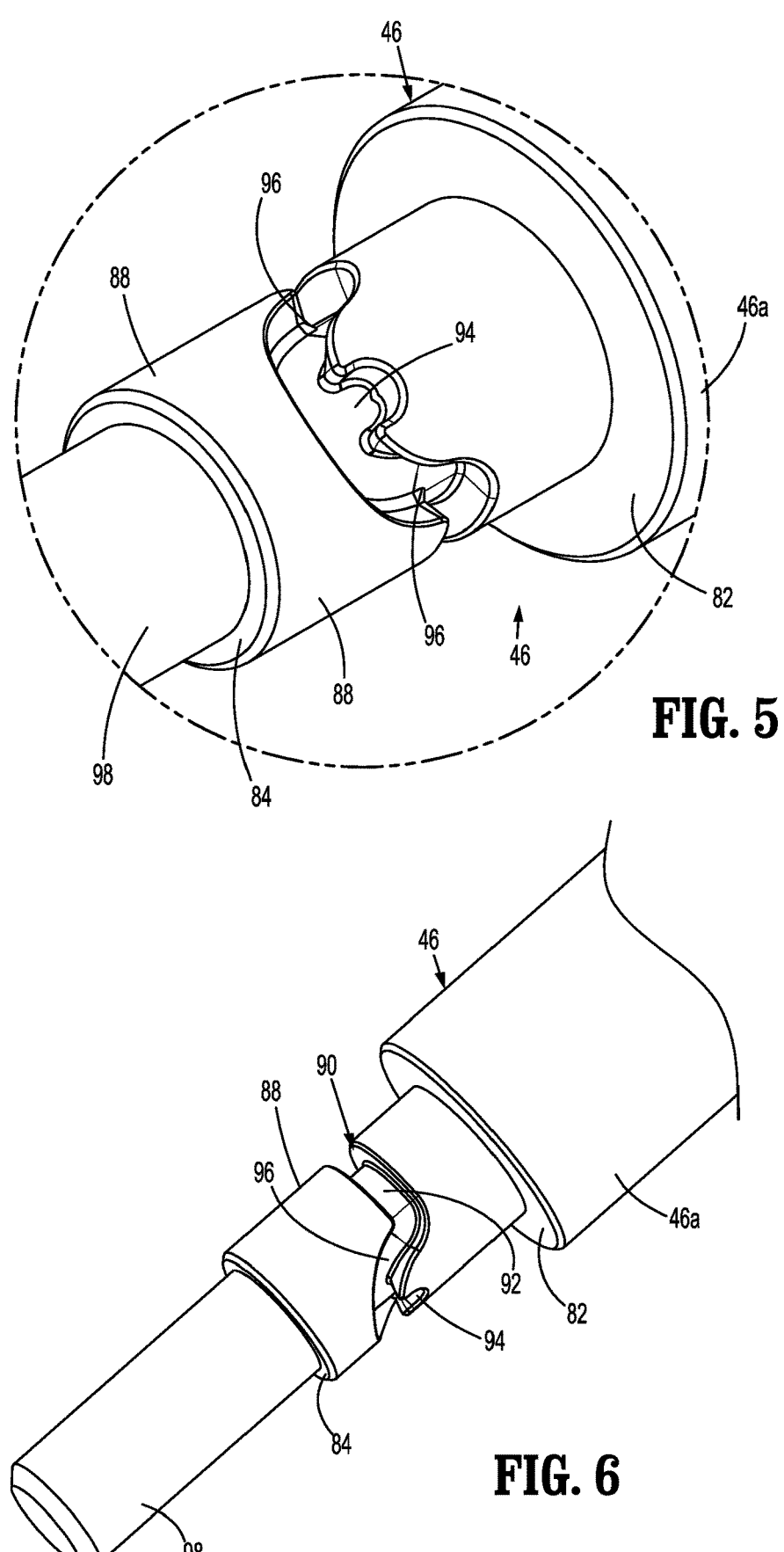
FIG. 5 is an enlarged view of the indicated area of detail shown in FIG. 2 illustrating a portion of a rotary cam of the rotary stitching device shown in FIG. 1.
FIG. 6 is a side perspective view of a distal portion of the rotary cam shown in FIG. 5.
Figures 7, 8:
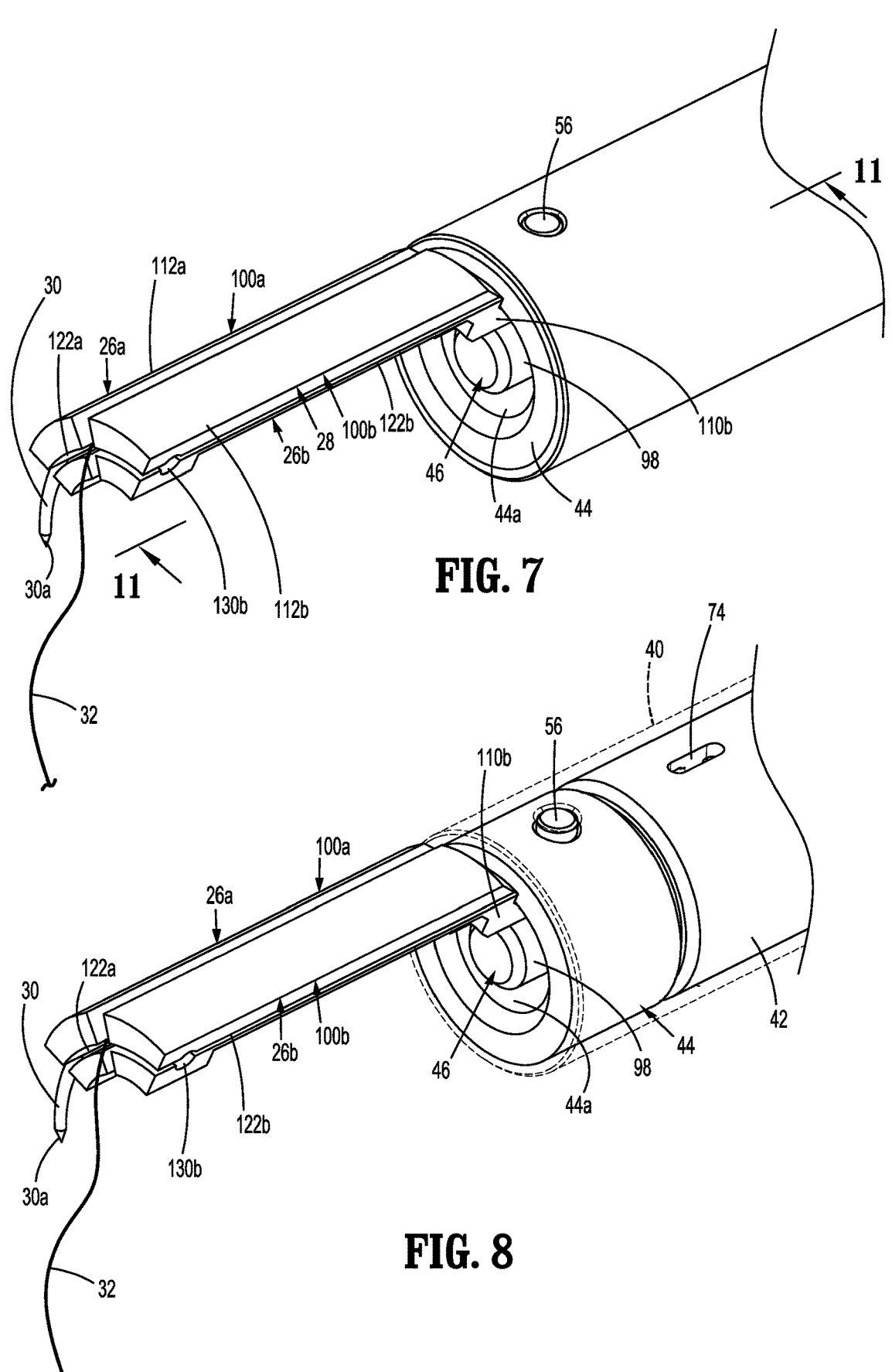
FIG. 7 is an enlarged view of the indicated area of detail shown in FIG. 2 illustrating a distal portion of the rotary stitching device in an initial position.
FIG. 8 is a side perspective view of the distal portion of the rotary stitching device shown in FIG. 7 with an outer tube of an elongate body assembly of the rotary stitching device shown in phantom.
Figures 9, 10:
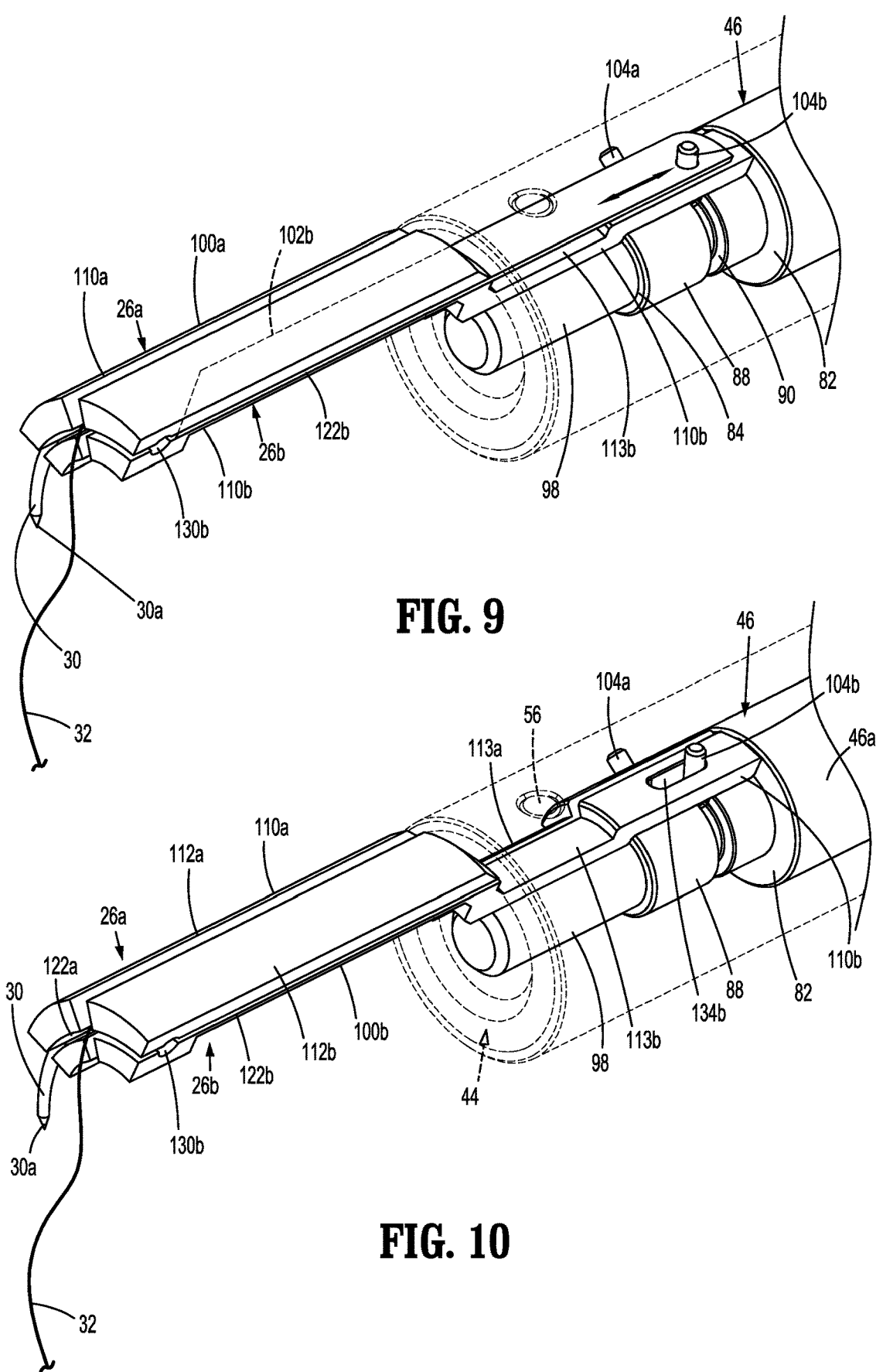
FIG. 9 is a side perspective view of the distal portion of the rotary stitching device shown in FIG. 8 with the outer tube, a fixed cam, and a jaw collar of the elongate body assembly of the rotary stitching device shown in phantom.
FIG. 10 is a side perspective view of the distal portion of the rotary stitching device shown in FIG. 8 with the outer tube, the fixed cam, and the jaw collar of the elongate body assembly of the rotary stitching device shown in phantom and blades of first and second jaw members of an end effector removed.

FIGS. 2, 5, and 6 illustrate the rotary cam 46 which is rotatably received within the longitudinally extending bore 60 (FIG. 2) of the stationary cam 42. In aspects of the disclosure, the rotary cam 46 defines a longitudinal axis that is coaxial with the longitudinal axis "X" of the elongate body assembly 14. The rotary cam 46 includes a cylindrical body 46a having a distal portion that has a stepped configuration. The distal portion of the body 46a of the rotary cam 46 defines a first shoulder 80 (FIG. 2), a second shoulder 82, and a third shoulder 84. When the rotary cam 46 is received within the longitudinally extending bore 60 of the stationary cam 42, the first shoulder 80 engages the annular shoulder 66a (FIG. 11) on the inner wall 66 of the stationary cam 42, and the second and third shoulders 82 and 84, respectively, engage portions of the first and second jaw assemblies 26a and 26b of the end effector 16 as described in further detail below.

The distal portion of the body 46a of the rotary cam 46 includes an intermediate step 88 that is positioned between the second and third shoulders 82 and 84 (FIG. 2) of the distal portion of the rotary cam 46 and defines a second cam slot 90 that extends entirely about the intermediate step 88. The second cam slot 90 includes a circular slot portion 92 (FIG. 6), a longitudinal slot portion 94, and angled slot portions 96. The circular slot portion 92 of the second cam slot 90 extends about the majority of the circumference of the rotary cam 46 along a plane that is substantially transverse to the longitudinal axis "X" of the elongate body assembly 14. The longitudinal slot portion 94 of the second cam slot 90 extends in a direction substantially parallel to the longitudinal axis "X" of the elongate body assembly 14. The angled slot portions 96 of the second cam slot 90 extend between ends of the circular slot portion 92 and the longitudinal slot portion 94 in directions oblique to the longitudinal axis "X". The second cam slot 90, in conjunction with the first cam slot 70 of the stationary cam 42, is configured to control operation of the end effector 16 as described in further detail below. The distal portion of the body 46a of the rotary cam 46 also includes a distal step 98 (FIG. 2).

FIGS. 2 and 7-11 illustrate the end effector 16 which includes the first and second jaw assemblies 26a, 26b. Each of the first and second jaw assemblies 26a and 26b includes a jaw member 100a, 100b, a blade 102a, 102b (FIG. 2), and a pin 104a, 104b. Each of the jaw members 100a, 100b includes a body that has a proximal portion 110a, 110b that is received within the outer tube 40 and the jaw collar 44 and a distal portion 112a, 112b that extends from the outer tube 40. The proximal portion 110a, 110b of each of the jaw members 100a, 100b includes a stepped inner surface 111a, 111b and an outer surface that defines a cavity 113a, 113b. Each of the stepped inner surfaces 111a, 111b forms a proximally facing shoulder 115a, 115b (FIG. 11) that is positioned at a proximal end of the inner surface 111a, 111b. The shoulders 115a, 115b of each of the jaw members 100a, 100b is engaged with the third shoulder 84 (FIG. 2) of the rotary cam 46. The stepped inner surfaces 111a, 111b of the jaw members 100a, 100b are supported on the distal step 98 of the distal portion of the rotary cam 46 at a position distal of the third shoulder 84 of the rotary cam 46 such that each of the jaw members 100a, 100b can rotate in relation to and about the rotary cam 46.

Figures 11, 12:
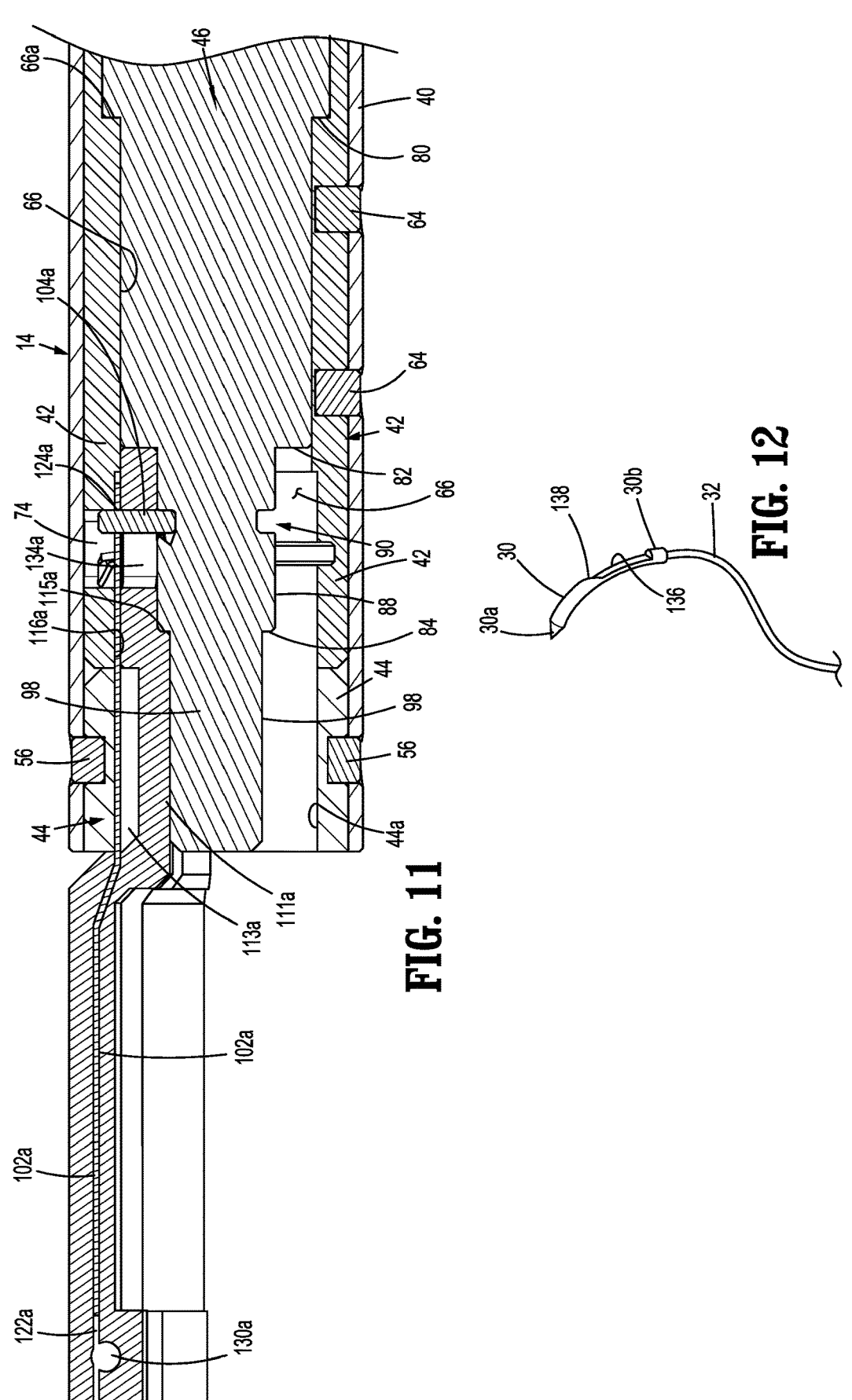
FIG. 11 is a cross-sectional view taken along section line 11-11 of FIG. 7.
FIG. 12 is an enlarged view of the indicated area of detail shown in FIG. 2 illustrating a needle and suture of the rotary stitching device.
Figure 13A:
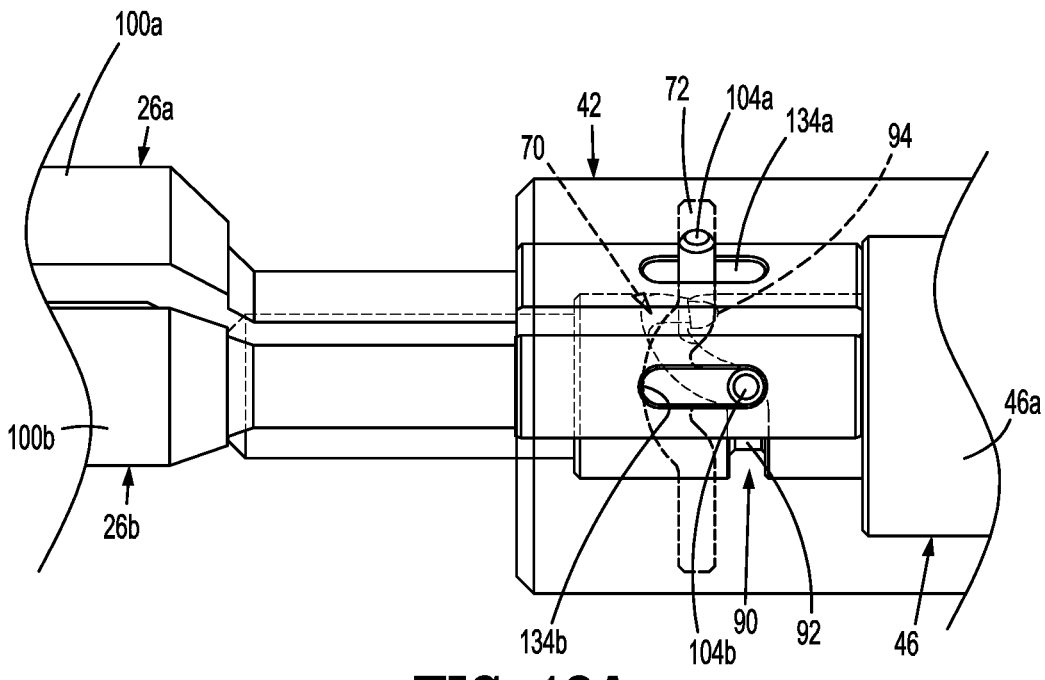
FIG. 13A is a side view of the distal portion of the elongate body assembly and a proximal portion of the end effector of the rotary stitching device shown in FIG. 1 in the initial position with the outer tube and jaw collar of the elongate body assembly and the blades of the end effector removed.
Figure 13B:
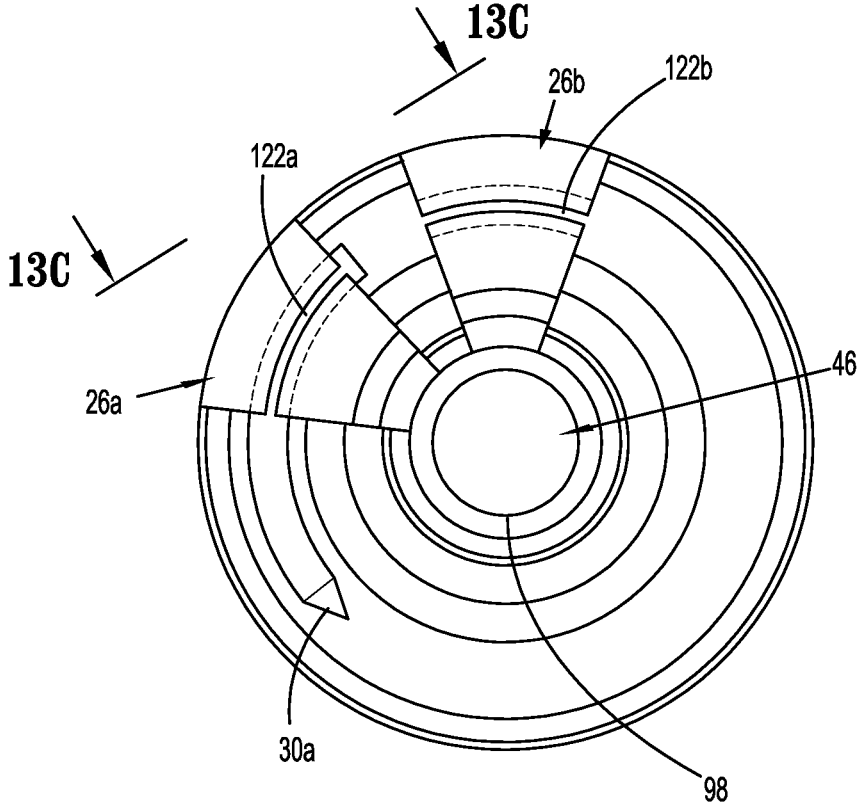
FIG. 13B is a view from a distal end of the rotary stitching device shown in FIG. 13A in the initial position.
Figure 13C:
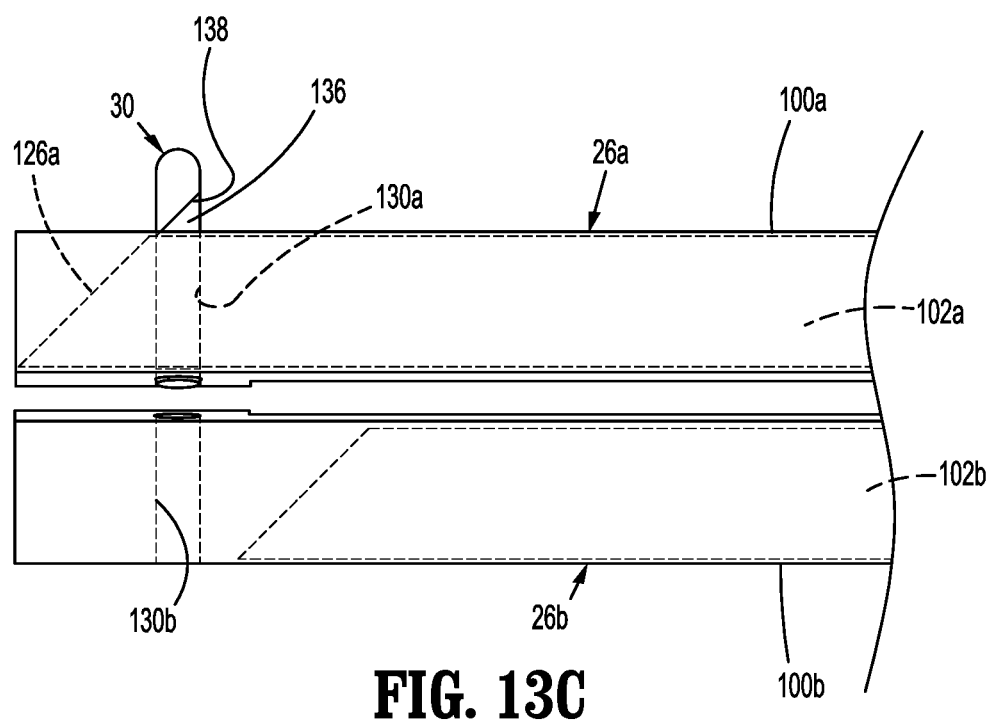
FIG. 13C is a view of the distal portion of the end effector view taken along line 13C-13C of FIG. 13B.
Figure 14A:
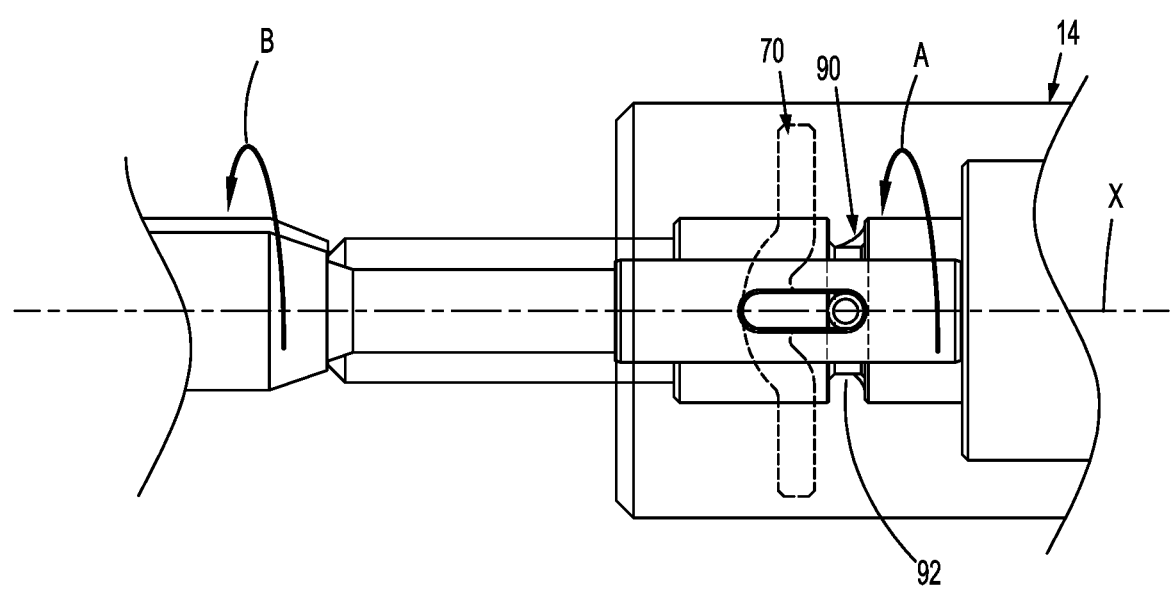
FIG. 14A is a side cutaway view of the distal portion of the elongate body assembly and the proximal portion of the end effector shown in FIG. 1, with the outer tube and the jaw collar of the elongate body assembly removed, in a partially actuated position illustrating the first jaw of the end effector as the first jaw begins to rotate towards the second jaw which is stationary.
Figure 14B:
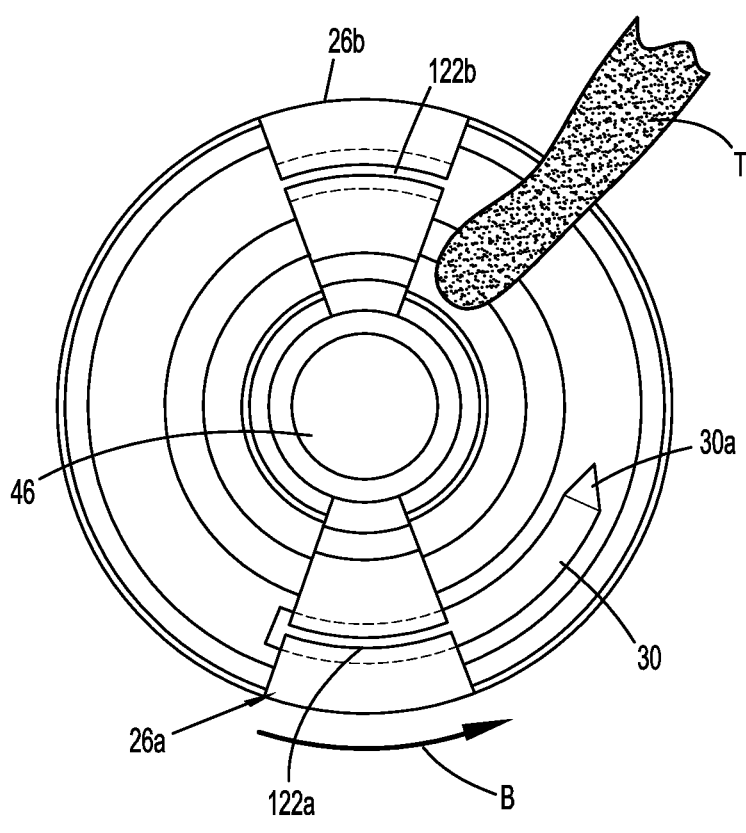
FIG. 14B is a view from the distal end of the rotary stitching device with the end effector in the position shown in FIG. 14A.

The jaw collar 44 is partially received within the cavities 113a, 113b of the jaw members 100a, 100b to secure the jaw members 100a, 100b at a longitudinally fixed position on the distal step 98 of the distal portion of the rotary cam 46 (FIG. 11). The proximal portion 110a, 110b of each of the jaw members 100a, 100b extends through the longitudinal bore 44a of the jaw collar 44 and is positioned in spaced relation to the inner surface 66 of the stationary cam 42 to define a channel 116a (FIG. 11, only one is shown)) between the inner surface 66 of the stationary cam 42 and the proximal portion 110a, 110b of each of the jaw members 100a, 100b.

The distal portion 112a, 112b of each of the jaw members 100a, 100b projects distally from the outer tube 40 of the elongate body assembly 14 and defines a longitudinally extending channel 122a, 122b (FIG. 2). Each of the longitudinally extending channels 122a, 122b receives one of the blades 102a, 102b. The blades 102a, 102b extend through the channels 116a (FIG. 11, only one is shown) defined between the inner surface 66 of the stationary cam 42 and an outer surface of the proximal portions 110a, 110b of each of the jaw members 100a, 100b and through the longitudinally extending channels 122a, 122b of the jaw members 100. Each of the blades 102a, 102b has a proximal portion that defines an opening 124a, 124b and a distal portion having an angled distal end 126a, 126b. The openings 124a, 124b in the blades 102a, 102b fixedly receive the pins 104a, 104b of the of the first and second jaw assemblies 26a, 26b such that the pins 104a, 104b extend outwardly form the respective blade 102a, 102b into the first cam slot 70 of the stationary cam 42 and inwardly from the blade 102a, 102b into the second cam slot 90 of the rotary cam 46.

The distal portion 112a, 112b of each of the jaw members 100a, 100b also defines an arcuate transverse bore 130a, 130b that intersects the respective longitudinally extending channel 122a, 122b defined by the jaw member 100a, 100b. The transverse bore 130a, 130b of each of the jaw members 100a, 100b receives the suture needle 30 as described below. The proximal portion 110a, 110b of each of the jaw members 100a, 100b defines a longitudinal slot 134a, 134b that receives a respective one of the pins 104a, 104b. When the pins 104a, 104b move through the first and second cam slots 70 and 90 of the stationary and rotary cams 42 and 46, respectively, the pins 104a, 104b are moved longitudinally within the longitudinal slots 134a, 134b of the jaw members 100a, 100b to move the blades 102a, 102b within the longitudinally extending channels 122a, 122b of the jaw members 100a, 100b between retracted and advanced positions. When the blades 102a, 102b are in the advanced position, the angled distal end 126a, 126b of the respective blade 102a, 102b projects distally from the channel 122a, 122b of the jaw member 100a, 100b into engagement with the suture needle 30 to secure the suture needle 30 to the respective blade 102a, 102b.

FIG. 12 illustrates the suture needle 30 which has a curved configuration and includes a first end 30a and a second end 30b. The first end 30a of the suture needle 30 is pointed or sharpened to facilitate piercing of tissue. The second end 30b of the suture needle 30 is coupled to the suture 32. The suture needle 30 defines a cutout 136 (FIG. 12) that is defined on one end by an angled cam surface 138 that is aligned with the angled distal end 126a, 126b (FIG. 2) of the respective blade 104a, 104b to which the suture needle 30 is to be attached. When the respective blade 104a, 104b is moved from its retracted position towards its advanced position, the angled distal end 126a, 126b of the respective blade 104a, 104b engages the angled cam surface 138 of the suture needle 30 to advance the suture needle 30 over a curved or arcuate path within the arcuate transverse bore 130a, 130b of the jaw member 100a, 100b such that the suture needle 30 projects from one side of the respective jaw member 100a, 100b. When the blade 104a, 104b is in the advanced position, the blade 104a, 104b is received within the cutout 136 of the suture needle 30 to fixedly secure the suture needle 30 in a position extending from the respective jaw member 100a, 100b.

FIG. 11-13C illustrate the distal portion of the elongate body assembly 14 and the proximal portion of the end effector 16 in an initial position. In the initial position, the first end of the pin 104a of the first jaw assembly 26a is positioned within the longitudinal slot portion 94 of the second cam slot 90 in the rotary cam 46 to releasably couple the first jaw assembly 26a to the rotary cam 46, and the second end of the pin 104a of the first jaw assembly 26a is received within a first end of the circular slot portion 72 of the first cam slot 70 of the stationary cam 42. The pin 104a is centrally located within the longitudinal slot 134a of the jaw member 100a of the first jaw assembly 26a such that the blade 102a is positioned within the cutout 136 (FIG. 12) of the suture needle 30 and extends from a side of the first jaw member 100a opposite to the second jaw member 100b. The first end of the pin 104b of the second jaw assembly 26b is received in a first end of the circular slot portion 92 of the second cam slot 90 of the rotary cam 46, and the second end of the pin 104b is received within the longitudinal slot portion 74 of the first cam slot 70 of the stationary cam 42. In this position, the first and second jaw assemblies 26a and 26b are positioned adjacent one another (FIG. 13B) and the first jaw member 26a is an active jaw and is rotatable about the longitudinal axis "X" of the elongate body assembly 14 (FIG. 1) with the rotary cam 46. In contrast, the second jaw member 26b is a passive jaw and is rotatably fixed to the stationary cam 42 by the second pin 104b.

Figure 15A:
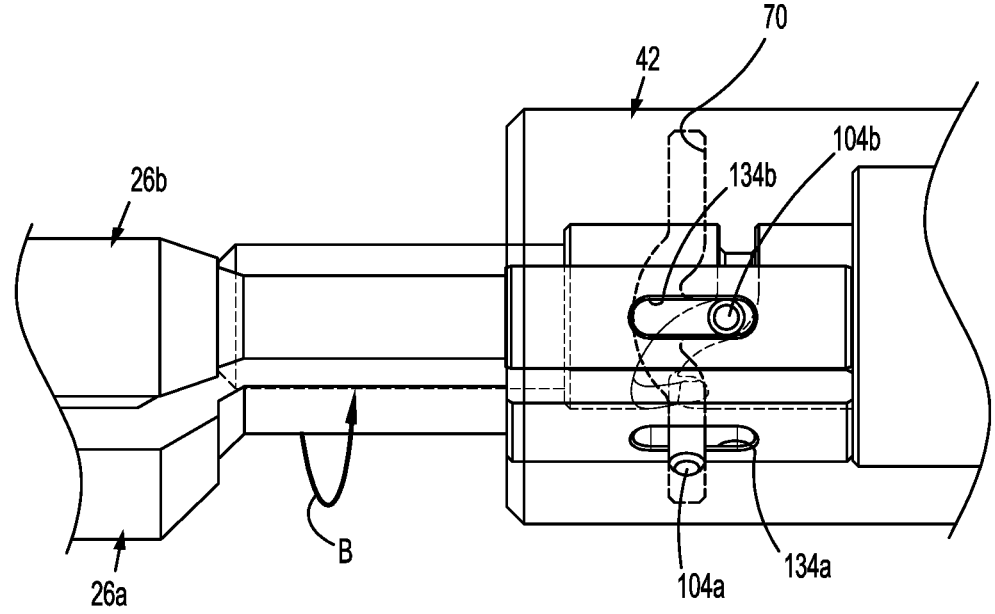
FIG. 15A is a side, cutaway view of the distal portion of the elongate body assembly and the proximal portion of the end effector of the rotary stitching device shown in FIG. 14A as the first jaw moves further toward the stationary second jaw.
Figure 15B:
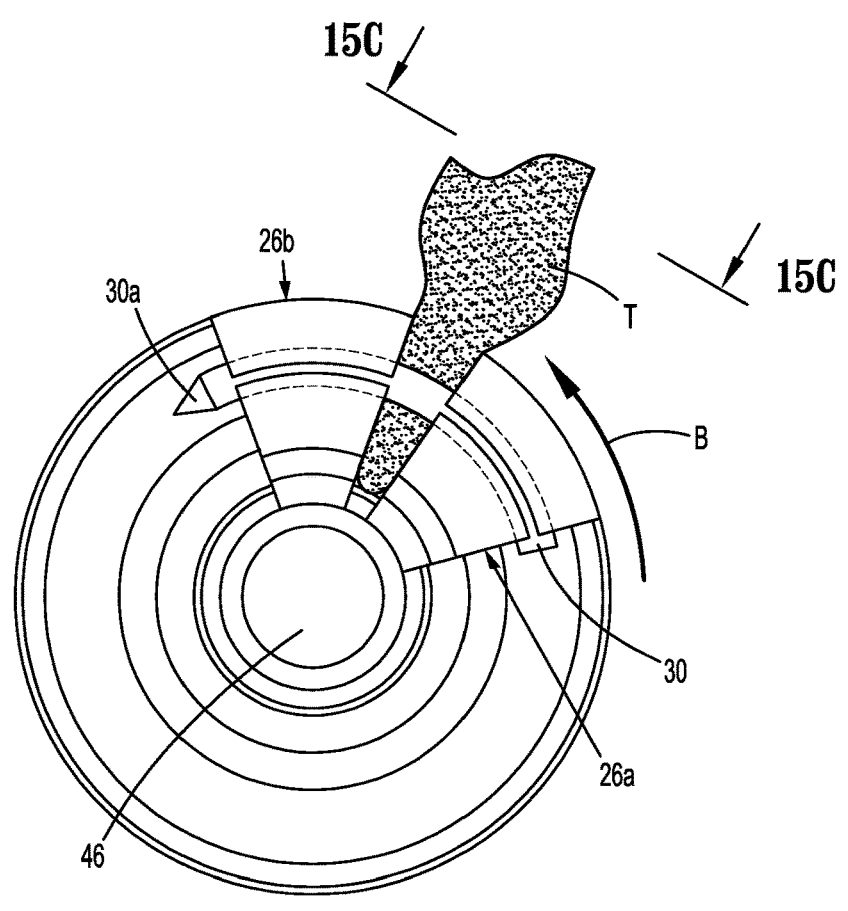
FIG. 15B is a view from the distal end of the rotary stitching device with the end effector in the position shown in FIG. 15A.
Figure 15C:
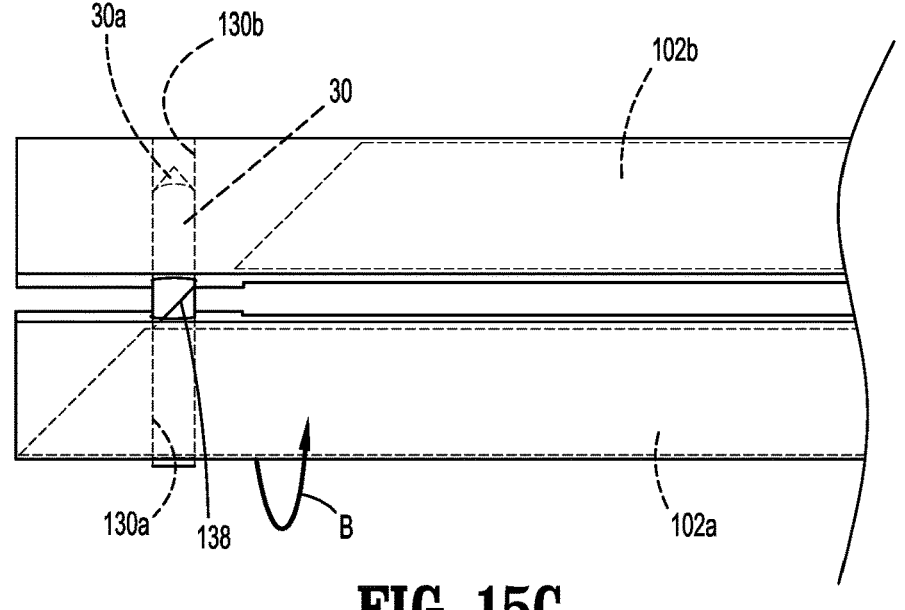
FIG. 15C is a side view as viewed from line 15C-15C of FIG. 15B.

FIGS. 14A-15C illustrate the stitching device 10 (FIG. 1) as the stitching device 10 is actuated by pressing the actuation buttons 22 on the handle assembly 12. When the stitching device 10 is actuated, the rotary cam 46 is rotated about the longitudinal axis "X" (FIG. 14A) of the elongate body assembly 14 of the stitching device 10 (FIG. 1) in the direction of arrows "A". Since the pin 104a of the first jaw assembly 26a is received within the longitudinal slot portion 94 of the second cam slot 90 in the rotary cam 46, the first jaw assembly 26a operates as the active jaw and rotates with the rotary cam 46 in the direction of arrow "B" (FIG. 14B) about the longitudinal axis "X" of the elongate body assembly 14 (FIG. 1) in a circular pattern. The second jaw assembly 26b operates as the passive jaw and remains stationary with one end of the pin 104b of the second jaw assembly 26b positioned within the longitudinal slot portion 74 of the stationary cam 42 and the other end of the pin 104b moving through the circular slot portion 92 of the second cam slot 90 of the rotary cam 46 as the rotary cam 46 is rotated about the longitudinal axis "X" of the elongate body assembly 14 (FIG. 1). As illustrated in FIG. 14B, tissue "T" is positioned between sides of the first and second jaw assemblies 26a, 26b in the path of the suture needle 30 which is secured to the first jaw assembly 26a by the blade 102a (FIG. 13C) which is in its advanced position. As the suture needle 30 engages the tissue "T" and continues to rotate in the direction of arrow "B" (FIGS. 14B and 15B), the tip 30a of the suture needle 30 pierces the tissue "T" and moves into the transverse bore 130b defined in the second jaw member 100b (FIG. 15C).

FIGS. 16A-20C illustrate the distal portion of the stitching device 10 as the first jaw assembly 26a and the second jaw assembly 26b switch positions between passive and active, i.e., the first jaw assembly 26a becomes the passive jaw and the second jaw assembly 26b becomes the active jaw.

Figure 16A:
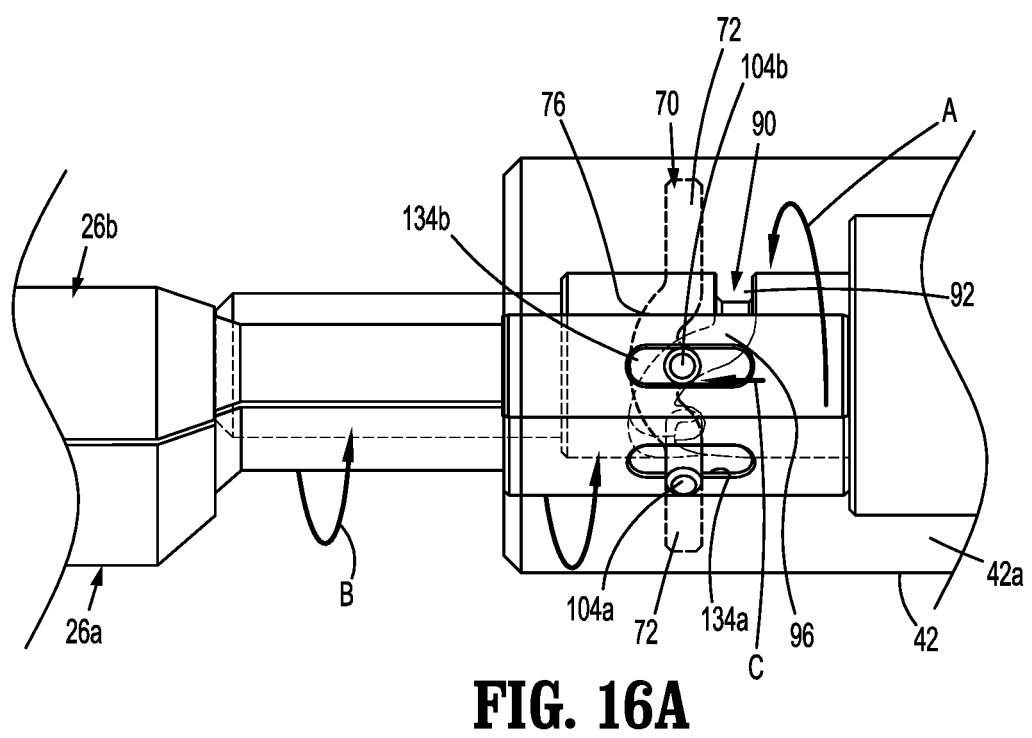
FIG. 16A is a side view of the distal portion of the elongate body assembly and the proximal portion of the end effector of the rotary stitching device shown in FIG. 1 with the outer tube and the jaw collar of the elongate body assembly and the blades of the end effector removed as the first jaw moves further towards the stationary second jaw and the stationary second jaw begins to unlock from the stationary cam.
Figure 16B:
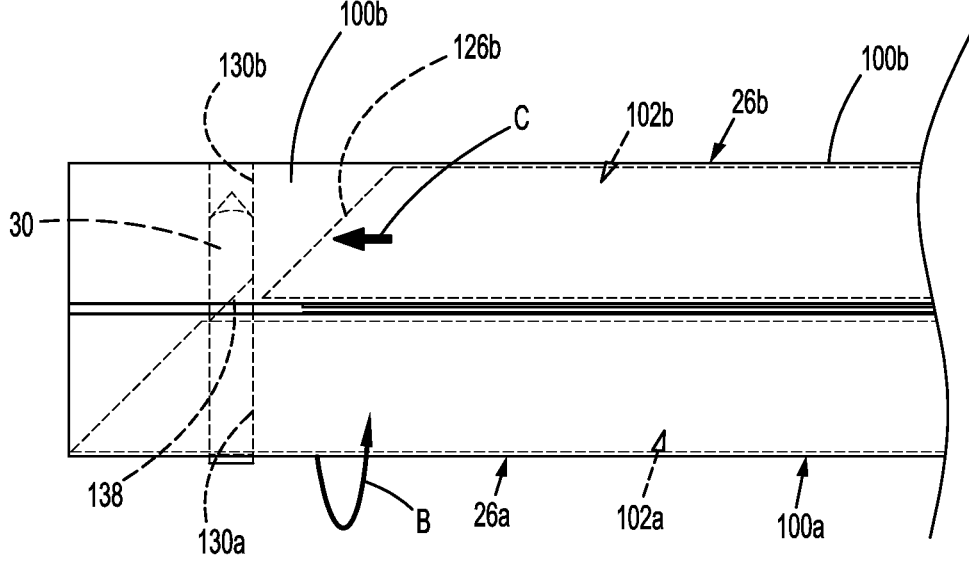
FIG. 16B is a side view of the distal portion of the end effector shown in FIG. 16A with the blades of the first and second jaw members shown in phantom as the blade of the second jaw moves towards the suture needle.

FIG. 16A illustrates the first jaw assembly 26a, which is the active jaw, as the first jaw assembly 26a moves into close approximation with the second jaw assembly 26b, which is the passive jaw. As the rotary cam 46 moves in the direction of arrow "A", the pin 104b moves into the angled slot portion 96 of the second cam slot 90 of the rotary cam 46 and begins to advance within the longitudinal slot portion 74 of the stationary cam 42 (FIG. 4) and within the longitudinal slot 134b of the jaw member 100b to begin to advance the blade 102b in the direction of arrow "C" in FIG. 16B through the longitudinally extending channel 122b of the jaw member 100b. As described above, the suture needle 30 is received within the transverse bore 130b in the jaw member 100b at a position in which the angled cam surface 138 of the suture needle 30 is aligned with the angled distal end of the blade 102b.

Figure 17:
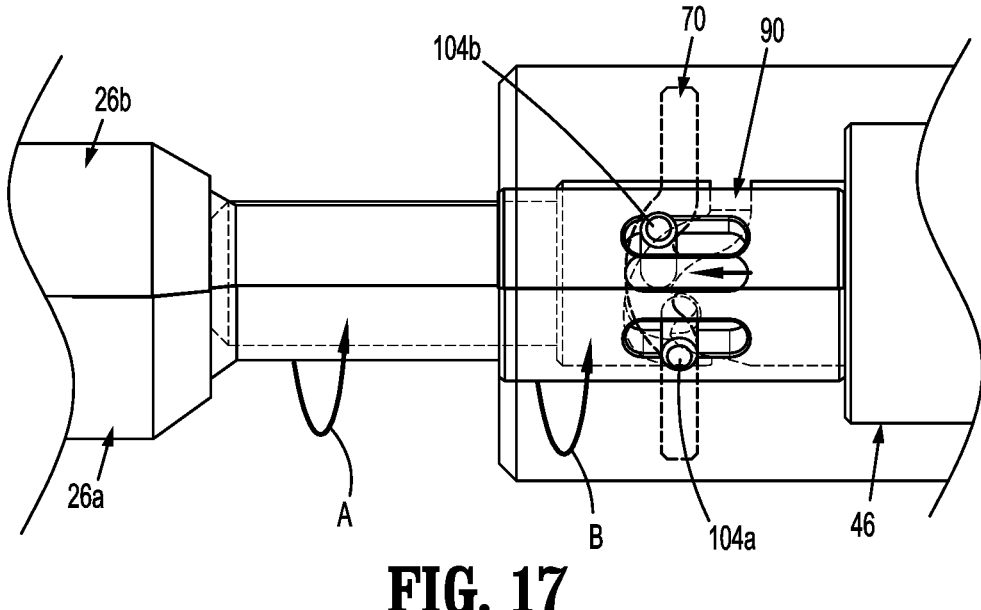
FIG. 17 is a side view of the distal portion of the elongate body assembly and the distal portion of the end effector shown in FIG. 1 with the outer tube and the jaw collar of the elongate body assembly removed with the second jaw unlocked from the stationary cam and the first and second jaw members rotating together back towards the initial position.

FIG. 17 illustrates the first jaw assembly 26a as the rotary cam 46 rotates the first jaw assembly 26a into engagement with the second jaw assembly 26b and begins to rotate the second jaw assembly 26b with the first jaw assembly 26a. It is noted, at this point of movement, the pin 104b is removed from the longitudinal slot portion 74 (FIG. 4) of the first cam slot 70 by the angled slot portion 96 of the second cam slot 90 of the rotary cam 46 such that the second jaw assembly 26b can rotate about the longitudinal axis "X" of the elongate body assembly 14 (FIG. 1). In this position, the pin 104a of the first jaw assembly 26a which is still the active jaw is received within the angled portion 96 of the second cam slot 90 of the rotary cam 46.

Figure 18:
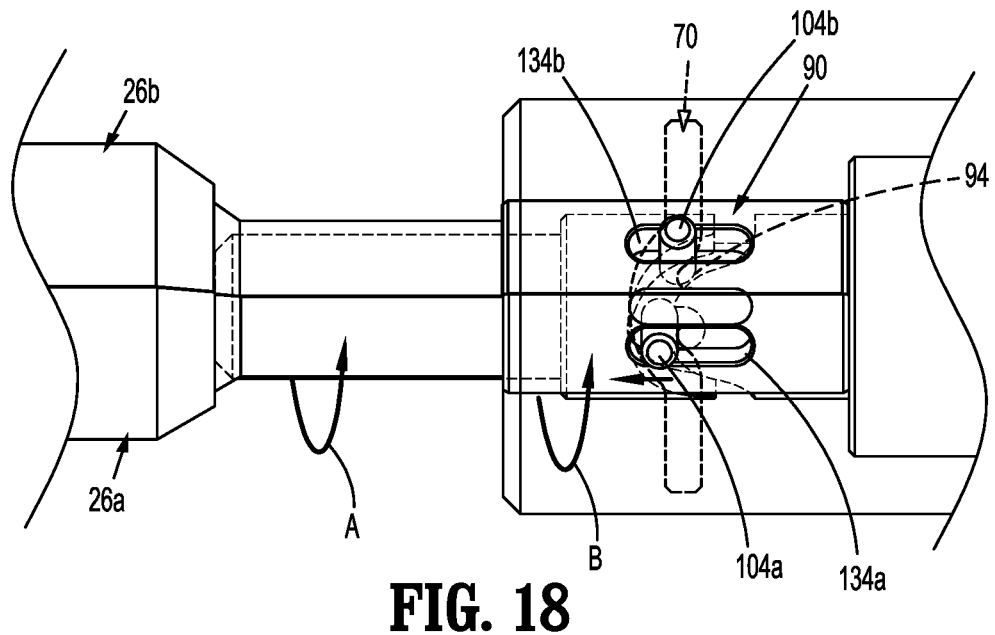
FIG. 18 is a side view of the distal portion of the elongate body assembly and the proximal portion of the end effector of the rotary stitching device shown in FIG. 1 as the stationary cam disengages the first jaw from the rotary cam.

FIG. 18 illustrates the point of operation of the stitching device 10 (FIG. 1) in which the pin 104*a* of the first jaw assembly 26*a* is disengaged from the rotary cam 46. As the rotary cam 46 continues to rotate, the angled slot portion 76 of the first cam slot 70 in the stationary cam 42 moves the pin 104*a* from within the longitudinal slot portion 94 (FIG. 5) of the rotary cam 46 to disengage the first jaw assembly 26*a* from the rotary cam 46.

Figure 19:
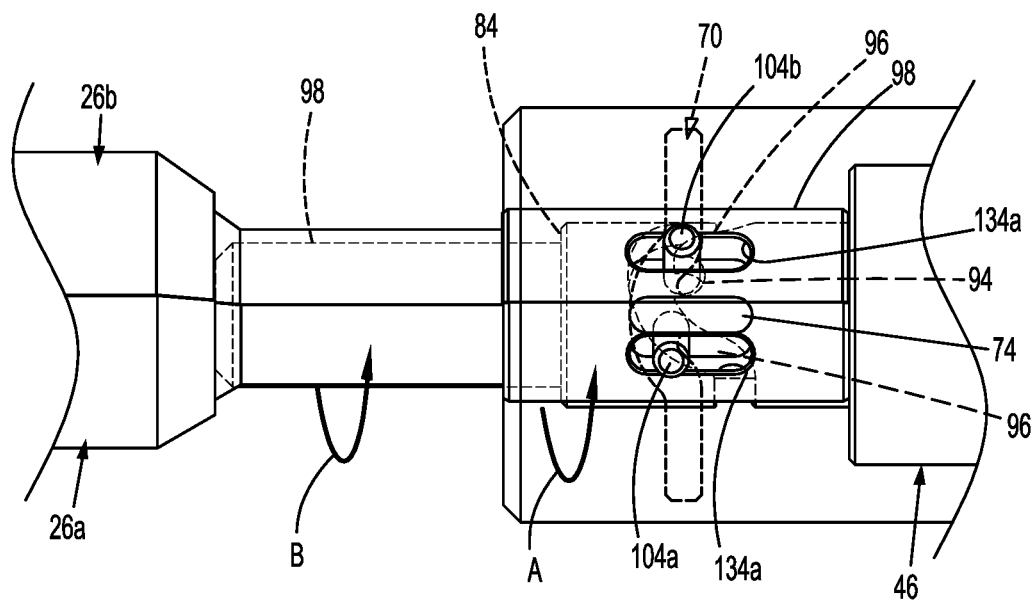
FIG. 19 is a side view of the distal portion of the elongate body assembly and the proximal portion of the end effector of the rotary stitching device shown in FIG. 1 as the stationary cam moves the second jaw into engagement with the rotary cam.

As illustrated in FIG. 19, as the rotary cam 46 continues to rotate, the angled slot portion 96 of the second cam slot 90 in the rotary cam 46 urges the pin 104*a* of the first jaw assembly 26*a* into the longitudinal slot portion 74 (FIG. 4) of the first cam slot 70 to rotatably fix the first jaw assembly 26*a* in relation to the stationary cam 42. As the pin 104*a* is retracted (or moves proximally) into the longitudinal slot portion 74 (FIG. 4) of the first cam slot 70, the blade 104*a* of the first jaw assembly 26*a* is retracted from within the cutout 136 (FIG. 12) of the suture needle 30 in the direction of arrow "D" in FIG. 20C to release the suture needle 30 from the jaw member 100*a* of the first jaw assembly 26*a*. In this position, the first jaw assembly 26*a* becomes the passive or stationary jaw.

Figure 20A:
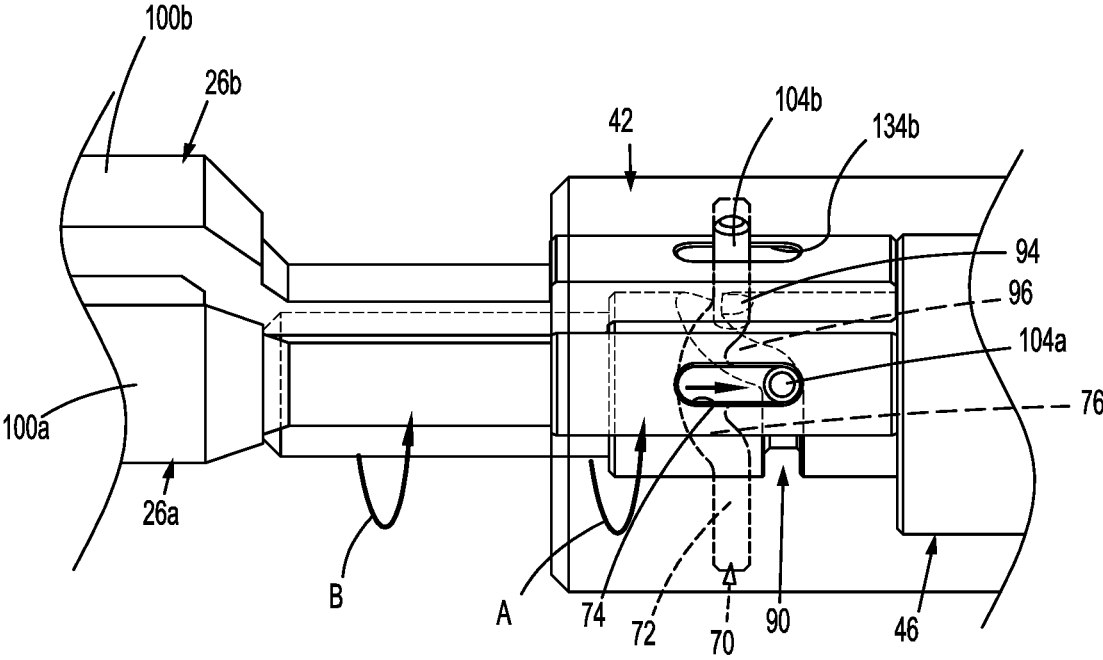
FIG. 20A is a side view of the distal portion of the elongate body assembly and the proximal portion of the end effector of the rotary stitching device shown in FIG. 1 with the outer tube and the jaw collar of the elongate body assembly removed illustrating the second jaw of the end effector as the second jaw begins to move with the rotary cam.

As illustrated in FIG. 20A, as the rotary cam 46 rotates, one of the angled slot portions 76 of the first cam slot 70 in the stationary cam 42 urges the pin 104*b* of the second jaw assembly 26*b* slightly proximally into the longitudinal slot portion 94 of the second cam slot 90 of the rotary cam 46 to releasably secure the second jaw assembly 26*b* to the rotatable cam 46 such that the second jaw assembly 26*b* becomes the active jaw. The angled slot portion 96 of the rotary cam 46 urges the pin 104*a* of the first jaw assembly 26*a* further into the longitudinal slot portion 74 (FIG. 4) of the first cam slot 70 to fully retract the blade 102*a* within the longitudinal channel 122*a* of the first jaw 100*a* of the first jaw assembly 26*a*.

Figure 20B:
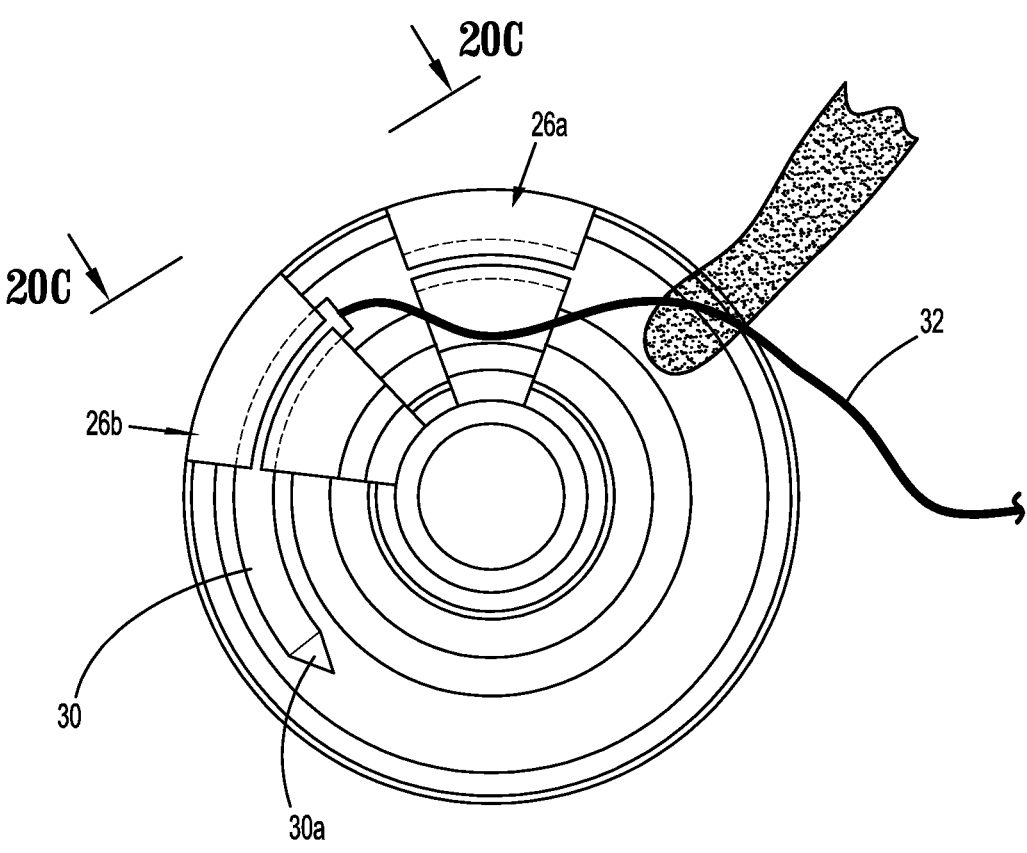
FIG. 20B is a view from a distal end of the rotary stitching device with the end effector in the position shown in FIG. 20A.
Figure 20C:
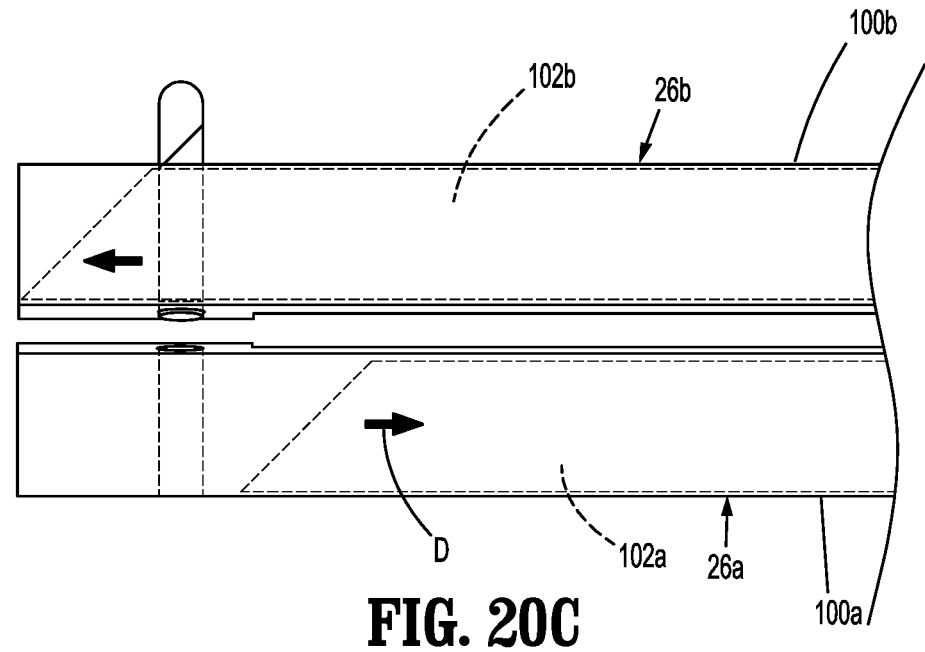
FIG. 20C is a view from the distal portion of the end effector view taken along line 20C-20C of FIG. 20B with the blade of the second jaw engaged with the suture needle and the blade of the first jaw disengaged from the suture needle.

FIG. 20B illustrates the second jaw assembly 26*b* as the second jaw assembly 26*b* moves with the rotary cam 46 to pull the suture 32 through the tissue "T". As shown, the first and second jaw assemblies 26*a*, 26*a* alternatingly move through a substantially 360-degree path to apply stitches through the tissue "T" in a manner that mimics traditional suturing techniques. It is noted that the active jaw rotates about the longitudinal axis "X" of the elongate body assembly 14 to the starting position of the passive jaw. As described above, the first jaw member 26*a* rotates to the initial position of the second jaw 26*b*. During this rotation, the second jaw member 26*b* is engaged by the first jaw member 26*a* and moved to the initial position of the first jaw member 26*a* before becoming the active jaw. Although this is not a full revolution about the longitudinal axis "X", or is less than 360-degrees of movement, this is a substantially full revolution as used herein.

The rotary cam 46 can be rotated through multiple revolutions to repeat the process described above. It is noted that the actuation buttons 22 (FIG. 1) and circuitry within the handle assembly 12 can be designed and configured such that each operation of a selected actuation button 22 can affect a single revolution of the rotary cam 46 to apply a suture to tissue. The actuation button 22 can be actuated multiple times to apply multiple sutures to tissue "T".

Persons skilled in the art will understand that the devices and methods specifically described herein and illustrated in the accompanying drawings are non-limiting exemplary aspects of the disclosure. It is envisioned that the elements and features illustrated or described in connection with one exemplary aspect of the disclosure may be combined with the elements and features of another without departing from the scope of the disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A suturing device comprising:
a handle assembly;
an elongate body assembly coupled to the handle assembly and defining a longitudinal axis, the elongate body assembly including a stationary cam and a rotary cam, the stationary cam defining a first cam slot and the rotary cam defining a second cam slot, the rotary cam including a stepped distal portion defining an annular shoulder between a distal step and an intermediate step positioned proximally of the distal step, the second cam slot being formed on the intermediate step, the rotary cam being rotatable in relation to the stationary cam; and
an end effector including a first jaw member and a second jaw member, the first and second jaw members including a distal portion and a proximal portion, the proximal portion of each of the first and second jaw members defining a proximally facing shoulder, the proximally facing shoulders of the first and second jaw members being engaged with the annular shoulder of the rotary cam, the first jaw member supporting a first pin and the second jaw member supporting a second pin, the first and second pins received within the first and second cam slots, wherein the first and second cam slots are configured to releasably secure one of the first or second jaw members to the rotary cam such that the first and second jaw members rotate about the stationary cam in alternating fashion, wherein during each revolution of the rotary cam, the one of the first or second jaw members rotates with the rotary cam for a substantially full revolution while the other of the first or second jaw members remains stationary.

2. The suturing device of claim 1, wherein the stationary cam has a tubular configuration and defines a longitudinally extending bore, and the rotary cam has a cylindrical configuration and is rotatably received within the longitudinally extending bore of the stationary cam.

3. The suturing device of claim 2, wherein the stationary cam has an inner surface that defines the first cam slot, and the rotary cam has an outer surface that defines the second cam slot.

4. The suturing device of claim 3, further including an outer tube positioned about the stationary cam.

5. The suturing device of claim 4, wherein the proximal portions of the first and second jaw members being rotatably supported about the rotary cam.

6. The suturing device of claim 5, the proximal portion of each of the first and second jaw members being rotatably supported about the distal step.

7. The suturing device of claim 4, further including a jaw collar secured within the outer tube, the jaw collar engaging the proximal portion of the first and second jaw members to retain the proximal portion of the first and second jaw members within the outer tube.

8. The suturing device of claim 1, further including a suture needle, wherein each of the first and second jaw members defines a transverse bore, the suture needle being movable between the transverse bores of the first and second jaw members.

9. The suturing device of claim 8, further including first and second blades, wherein each of the first and second jaw members defines a longitudinally extending channel, the first blade received within the longitudinally extending channel of the first jaw member and the second blade received within the longitudinally extending channel of the second jaw member, the first and second blades movable within the longitudinally extending channels between retracted and advanced positions to secure the suture needle to a respective one of the first and second jaw members.

10. The suturing device of claim 9, wherein the first pin is secured to the first blade and the second pin is secured to the second blade, and the first and second cam slots are configured to move the first and second blades between their respective retracted and advanced positions.

11. The suturing device of claim 10, wherein the suture needle includes an angled cam surface and each of the first and second blades includes an angled distal end that is positioned to engage the angled cam surface of the suture needle when the first or second blade moves from the retracted position to the advanced position to translate the suture needle within the transverse bore of the first or second jaw member.

12. The suturing device of claim 11, wherein each of the first and second jaw members defines a longitudinal slot that receives one of the first and second pins.

13. The suturing device of claim 8, further including a suture attached to one end of the suture needle.

14. A suturing device comprising:
an elongate body assembly defining a longitudinal axis and including a stationary cam and a rotary cam, the stationary cam defining a first cam slot and the rotary cam defining a second cam slot, the rotary cam including a stepped distal portion defining an annular shoulder between a distal step and an intermediate step positioned proximally of the distal step, the second cam slot being formed on the intermediate step, the rotary cam being rotatable in relation to the stationary cam;
an end effector including a first jaw member and a second jaw member, the first and second jaw members including a distal portion and a proximal portion, the proximal portion of each of the first and second jaw members being rotatably supported about the distal step of the rotary cam and defining a proximally facing shoulder, the proximally facing shoulders of the first and second jaw members being engaged with the annular shoulder of the rotary cam, the first jaw member supporting a first pin and the second jaw member supporting a second pin, the first and second pins received within the first and second cam slots, wherein the first and second cam slots are configured to releasably secure one of the first or second jaw members to the rotary cam such that the first and second jaw members rotate about the stationary cam in alternating fashion, wherein during each revolution of the rotary cam, the one of the first or second jaw members rotates with the rotary cam for a substantially full revolution while the other of the first or second jaw members remains stationary; and
a suture needle movable between the first and second jaw members and securable to and movable with the one of the first or second jaw members.

15. The suturing device of claim 14, wherein the stationary cam has a tubular configuration and an inner surface that defines a longitudinally extending bore, and the rotary cam has a cylindrical configuration and an outer surface, the rotary cam being rotatably received within the longitudinally extending bore of the stationary cam, the first cam slot formed in the inner surface of the stationary cam and the second cam slot formed in the outer surface of the rotary cam.

16. The suturing device of claim 14, further including first and second blades, wherein each of the first and second jaw members defines a longitudinally extending channel, the first blade received within the longitudinally extending channel of the first jaw member and the second blade received within the longitudinally extending channel of the second jaw member, the first and second blades movable within the longitudinally extending channels between retracted and advanced positions to secure the suture needle to a respective one of the first and second jaw members.

17. The suturing device of claim 16, wherein the first pin is secured to the first blade and the second pin is secured to the second blade, and the first and second cam slots are configured to move the first and second blades between their respective retracted and advanced positions.

18. The suturing device of claim 14, further including a suture attached to one end of the suture needle.

19. A suturing device comprising:
an elongate body assembly defining a longitudinal axis and including a stationary cam and a rotary cam, the stationary cam defining a first cam slot and the rotary cam defining a second cam slot, the rotary cam including a stepped distal portion defining an annular shoulder between a distal step and an intermediate step positioned proximally of the distal step, the second cam slot being formed on the intermediate step, the rotary cam being rotatable in relation to the stationary cam;
an end effector including a first jaw member and a second jaw member, the first and second jaw members including a distal portion and a proximal portion, the proximal portion of each of the first and second jaw members defining a proximally facing shoulder, the proximally facing shoulders of the first and second jaw members being engaged with the annular shoulder of the rotary cam, the first jaw member supporting a first pin and the second jaw member supporting a second pin, the first and second pins received within the first and second cam slots, wherein the first and second cam slots are configured to releasably secure one of the first or second jaw members to the rotary cam such that the first and second jaw members rotate about the stationary cam in alternating fashion, wherein during each revolution of the rotary cam, the one of the first or second jaw members rotates with the rotary cam for a substantially full revolution while the other of the first or second jaw members remains stationary;
a suture needle movable between the first and second jaw members and securable to and movable with the one of the first or second jaw members; and
first and second blades;
wherein each of the first and second jaw members defines a longitudinally extending channel, the first blade received within the longitudinally extending channel of the first jaw member and the second blade received within the longitudinally extending channel of the second jaw member, the first and second blades movable between retracted and advanced positions to secure the suture needle to a respective one of the first and second jaw members.

20. The suturing device of claim 19, wherein each of the first and second jaw members defines a longitudinal slot that receives one of the first and second pins.

* * * * *